United States Patent [19]
Kaitoh et al.

[11] Patent Number: 5,260,443
[45] Date of Patent: Nov. 9, 1993

[54] PIPERIDINE DERIVATIVES AS PHOTOSTABILIZER

[75] Inventors: Mitsumasa Kaitoh; Hideki Kurokawa; Akiyoshi Ohnishi, all of Yokkaichi, Japan

[73] Assignee: Mitsubishi Petrochemical Company Limited, Tokyo, Japan

[21] Appl. No.: 931,023

[22] Filed: Aug. 17, 1992

Related U.S. Application Data

[62] Division of Ser. No. 893,021, Jun. 3, 1992, Pat. No. 5,189,172.

Foreign Application Priority Data

Jun. 3, 1991 [JP] Japan .................. 3-160134
Sep. 3, 1991 [JP] Japan .................. 3-250563
Sep. 3, 1991 [JP] Japan .................. 3-250564

[51] Int. Cl.⁵ .................. C07D 405/06; C07D 211/22
[52] U.S. Cl. .................. 546/214; 546/216; 546/221
[58] Field of Search .................. 546/207, 216, 214, 221

[56] References Cited

U.S. PATENT DOCUMENTS

| | | | |
|---|---|---|---|
| 4,075,165 | 2/1978 | Soma et al. | 546/207 |
| 4,131,599 | 12/1978 | Brunnetti et al. | 546/192 |
| 4,141,883 | 2/1979 | Soma et al. | 546/208 |
| 5,101,033 | 3/1992 | Kazmiesczak et al. | 546/208 |

*Primary Examiner*—C. Warren Ivy
*Assistant Examiner*—Celia Chang
*Attorney, Agent, or Firm*—Oblon, Spivak, McClelland, Maier & Neustadt

[57] ABSTRACT

Disclosed is a piperidine derivatives of a formula:

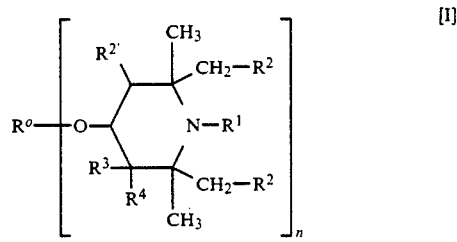

wherein
$R^0$ indicates a hydrogen atom or a group $R\!-\!(CO)_{\overline{n}}$ where R is an alkyl, alkylene or arylene group capable of having 1 to 4 carboxylic group;
$R^1$ indicates a hydrogen atom, an alkyl group having 1 to 4 carbon atoms, an acyl group having 2 to 7 carbon atoms, or an arylalkyl group having 7 to 10 carbon atoms;
$R^2$ and $R^{2'}$ respectively indicate a hydrogen atom, or an alkyl group having 1 to 4 carbon atoms;
$R^3$ and $R^4$ in combination indicate a group $=\!CH\!-\!R^5$, or $R^3$ indicates a hydrogen atom and $R^4$ indicates either $-\!CH_2\!-\!R^5$ wherein $R^5$ is a substituted or non-substituted phenyl group or a substituted or non-substituted cyclohexyl group the substituent being an alkyl having 1 to 4 carbon atoms, or a 2-furyl group or a tetrahydrofuryl group; and
n indicates an integer of 1 to 4.

The piperidine derivatives are improved photostabilizer to various organic materials including poly-α-olefins with least breeding out tendency.

4 Claims, 7 Drawing Sheets

PIPERIDINE DERIVATIVES AS PHOTOSTABILIZER

This is a division of application Ser. No. 07/893,021, filed on Jun. 3, 1992 now U.S. Pat. No. 5,189,172 issued on Feb. 23, 1993.

BACKGROUND OF THE INVENTION

1. Field of the Art

The present invention is concerned with piperidine derivatives of a novel structure.

More particularly, the present invention relates to 2,2,6,6-tetraalkylpiperidine derivatives which are useful as photostabilizers/lightstabilizer or as intermediates therefor and are also usable as intermediates for pharmaceuticals and agricultural chemicals.

2. Related Art

It has heretofore been known in the art that chemical compounds having a 2,2,6,6-tetraalkylpiperidine structure, viz. what is called hindered amine structure, have capability of capturing radicals at a high level, whereby these compounds have been used as photostabilizers for various organic materials, particularly resins.

The most typical hindered amine compounds having the photostabilizing capability may be 2,2,6,6-tetramethyl-4-piperidinol of a formula (1) which is often and hereinbelow abbreviated as TMPNL:

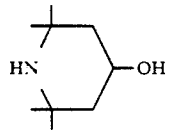
(1)

Most commercially available photostabilizers are derivatives of TMPNL in that it is used as an intermediate and is processed to have a higher molecular weight by, e.g. condensation with a polybasic carboxylic acid. For instance, as shown in Y. Nakahara et al: RECENT DEVELOPMENT IN ADDITIVES FOR HIGH POLYMERS (in Japanese), C.M.C. Corp. 1988, bis(2,2,6,6-tetramethyl-4-piperidyl)sebacate which is a representative photostabilizer known to have high photostabilizing capability to a lot of resins and hereinbelow referred to as LS770 is an ester of TMPNL with sebacic acid of a formula:

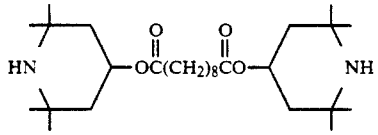
(2)

While the TMPNL derivatives representable by LS770 have high photostabilizing capability, they may have disadvantages such that they easily breed out from resin compositions to which they have been added whereby it may be difficult to use them in resin compositions for use as thin articles such as film, and even when they are used in resin compositions for use as thick articles, the surface of the articles may be deteriorated by the breeding out whereby coatability of the articles is deteriorated.

In order to solve these problems, various piperidine derivatives have heretofore been synthesized, such as a piperidinone derivative disclosed in Japanese Patent Publication No. 42987/1979 having a formula:

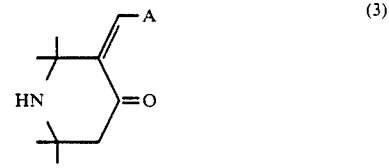
(3)

wherein $R^0$ is a phenyl group or a 2-furyl group.

The compound of formula (3) may have some disadvantages, as long as the present inventors know, such that it may be difficult to process it to have a higher molecular weight and the resin compositions having the compound added as a photostabilizer may be discolored when the compositions are fabricated.

SUMMARY OF THE INVENTION

The object of the present invention is to solve the problems inherent in the TMPNL derivatives shown above by presenting novel TMPNL derivatives modified in a specific way.

The present invention thus present a piperidine derivative of a formula:

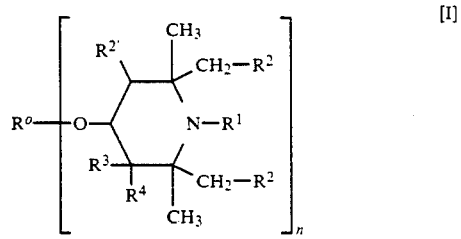
[I]

wherein:

$R^0$ indicates a hydrogen atom or a group $R+CO\!\!\!\!+_n$ where R is an alkyl, alkylene or arylene group capable of having 1 to 4 carboxylic group;

$R^1$ indicates a hydrogen atom, an alkyl group having 1 to 4 carbon atoms, an acyl group having 2 to 7 carbon atoms, or an arylalkyl group having 7 to 10 carbon atoms;

$R^2$ and $R^{2'}$ respectively indicate a hydrogen atom, or an alkyl group having 1 to 4 carbon atoms;

$R^3$ and $R^4$ in combination indicate a group $=CH-R^5$, or $R^3$ indicates a hydrogen atom and $R^4$ indicates $-CH_2-R^5$ wherein $R^5$ is either a substituted or non-substituted phenyl group or a substituted or non-substituted cyclohexyl group the substituent being an alkyl having 1 to 4 carbon atoms, or a 2-furyl group or a tetrahydrofuryl group; and n indicates an integer of 1 to 4.

The piperidine derivatives in accordance with the present invention have an aromatic ring in the molecule and thus have a higher solubility than the piperidine derivatives of the prior art in various organic materials including resins, such as polyolefins, e.g. polyethylene, polypropylene and polystyrene and a lower discoloring activity when they are kneaded with resins such as given above, whereby they are advantageously used as a photostabilizer as such or, when they are of a low molecular weight where $R^0$ is a hydrogen atom, as derivatives endowed with a higher molecular weight by esterification with mono- or polybasic carboxylic acid (other than R—(COOH)$_n$) with high photostabilization capability without entailing the breeding out.

The piperidine derivatives in accordance with the present invention has a hydroxyl group when $R^0$ is a hydrogen atom and an amino group when $R^1$ is a hydrogen atom, and it may be easy for converting the piperidine compounds into further derivatives in utilization of the hydroxyl and/or amino group.

The piperidine derivatives having substituents $R^3$ and $R^4$ in accordance with the present invention may have higher resistance to hydrolysis than the similar compounds having, however, no $R^3$ and $R^4$ substituents formed in most of conventional photostabilizers including TMPNL and LS770.

BRIEF DESCRIPTION OF THE DRAWINGS

FIG. A1 is a $^1$H-NMR spectrum for 3-benzyl-2,2,6,6-tetramethyl-4-piperidinol, Compound A1 prepared in Example A1;

FIG. A2 is a $^{13}$C-NMR spectrum by the proton decoupling method for 3-benzyl-2,2,6,6-tetramethyl-4-piperidinol, Compound A1 prepared in Example A1;

Figure 1A:
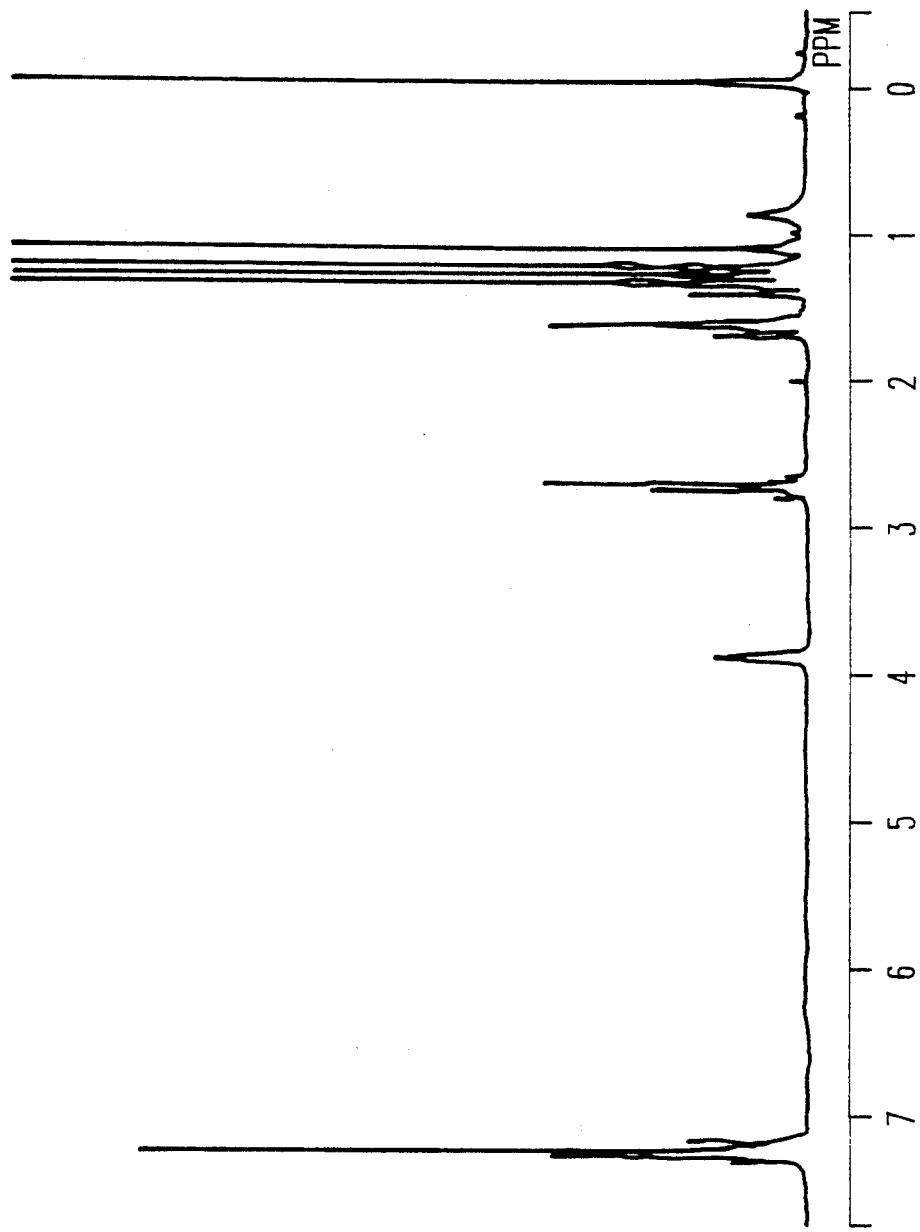
Figure 1B:
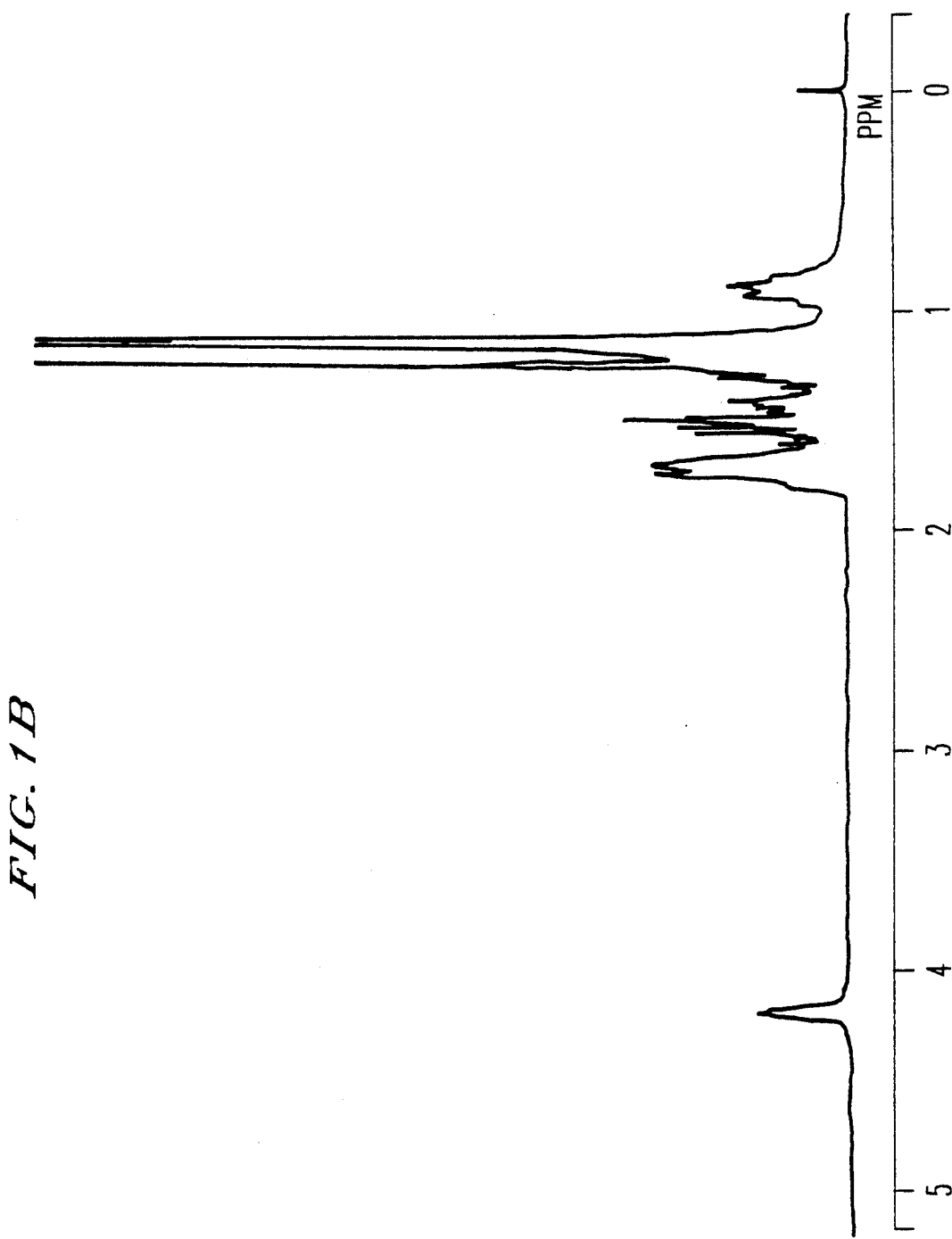
Figure 1C:
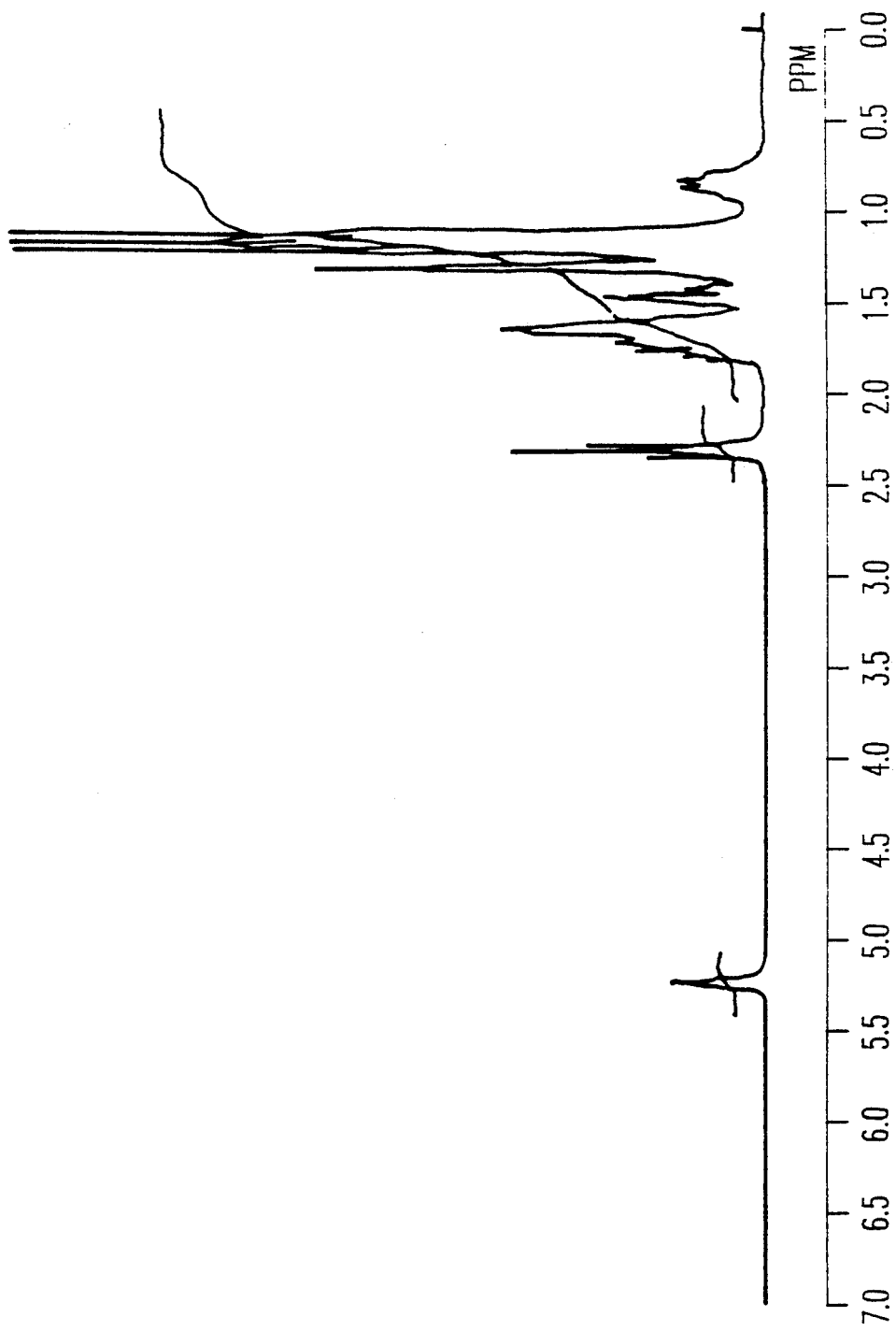
Figure 2A:
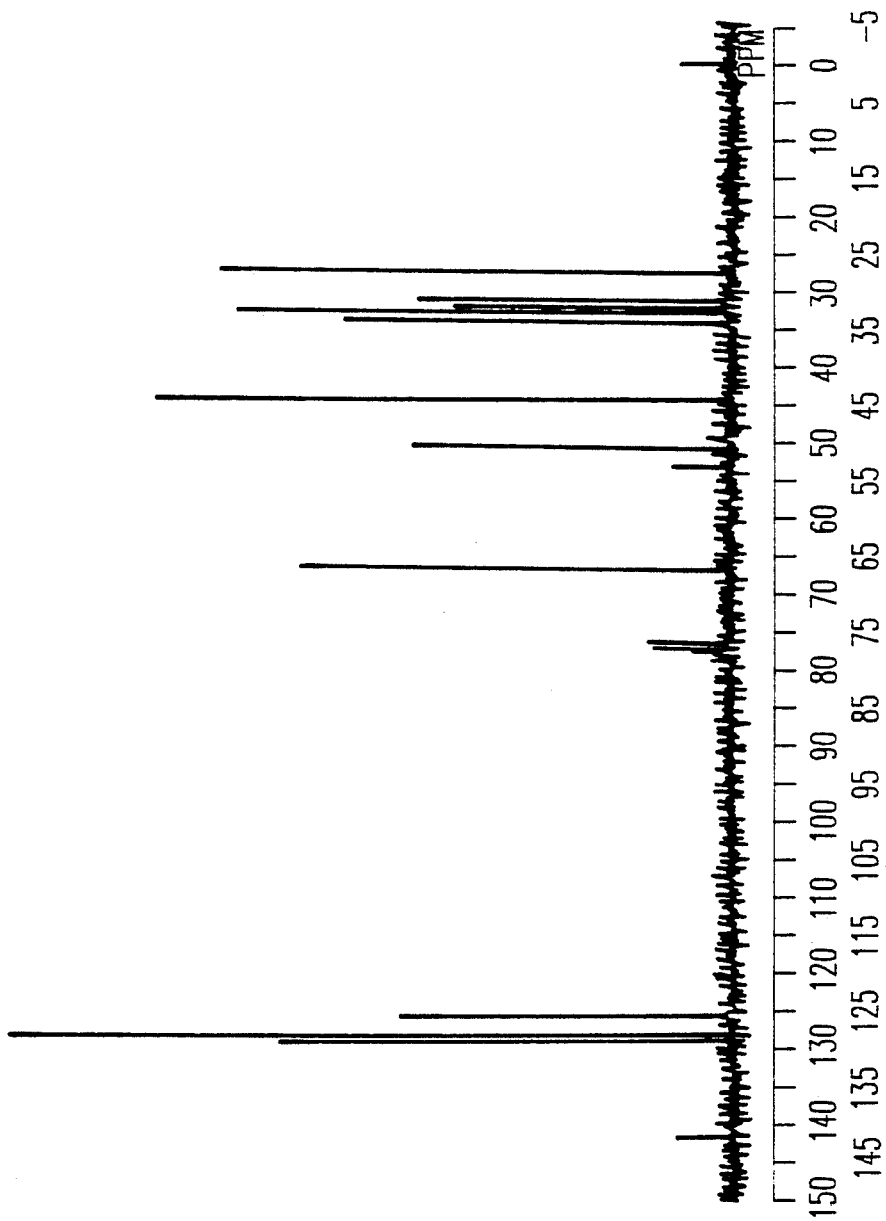
Figure 2B:
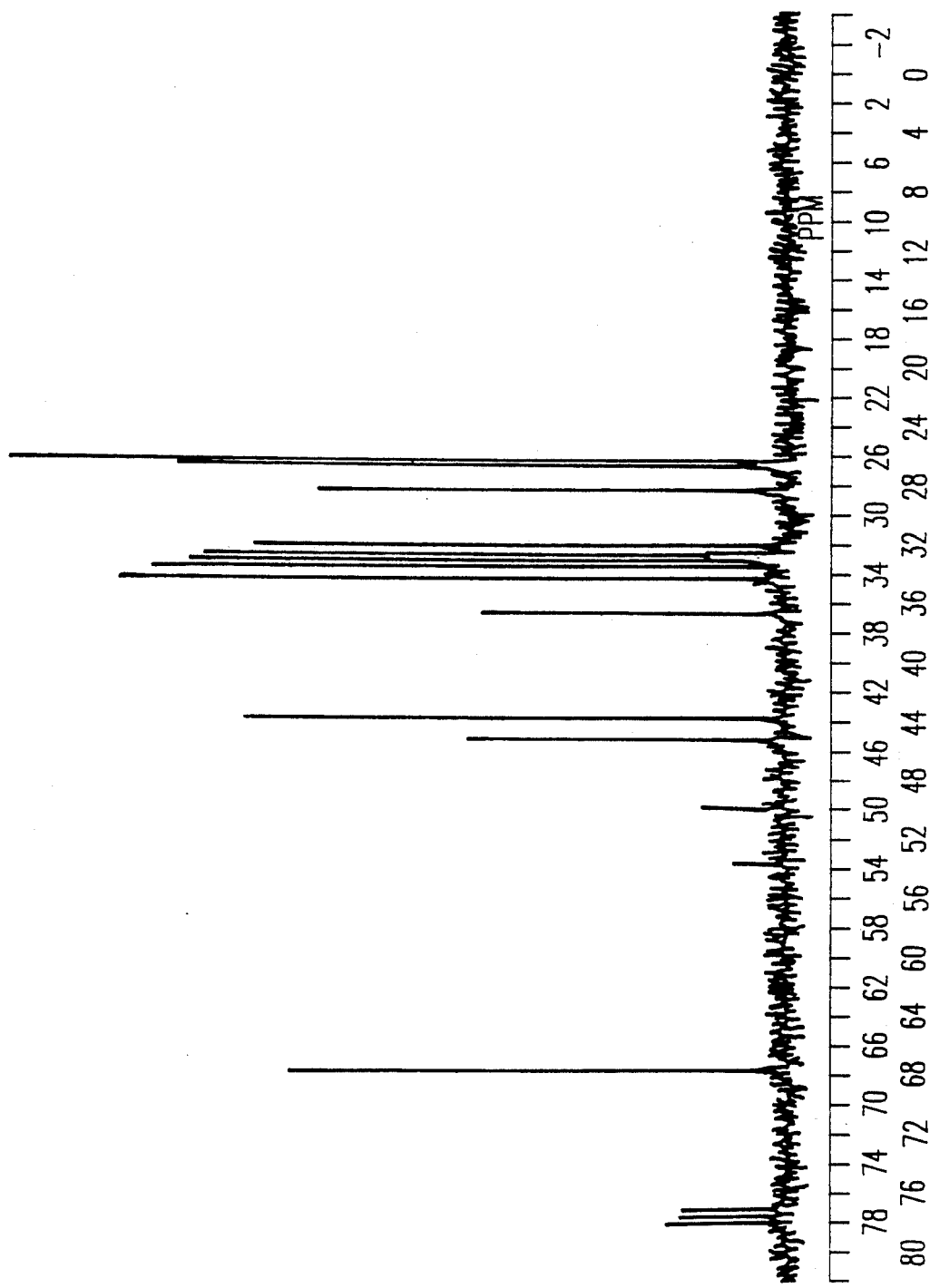
Figure 2C:
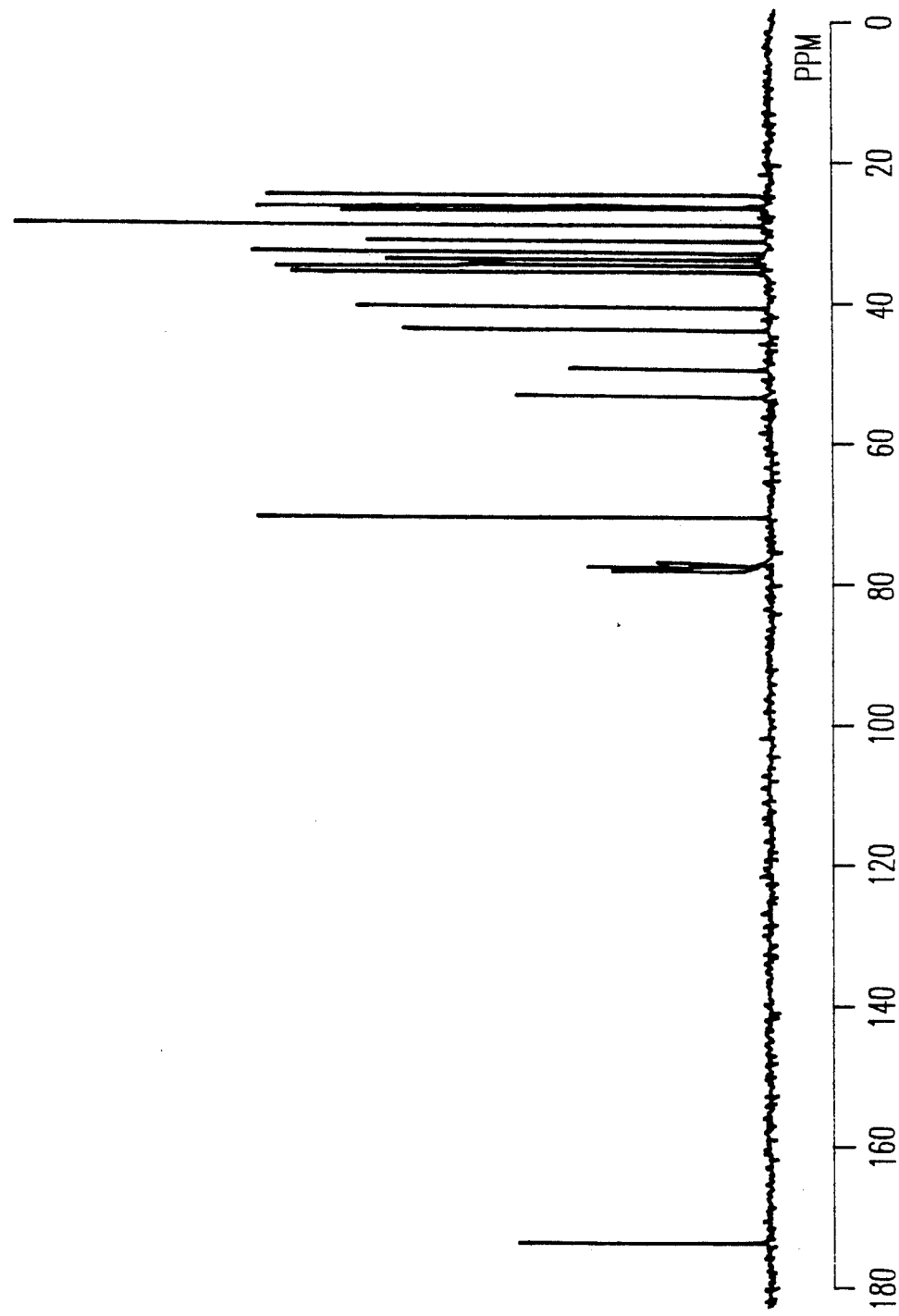
Figure 3:
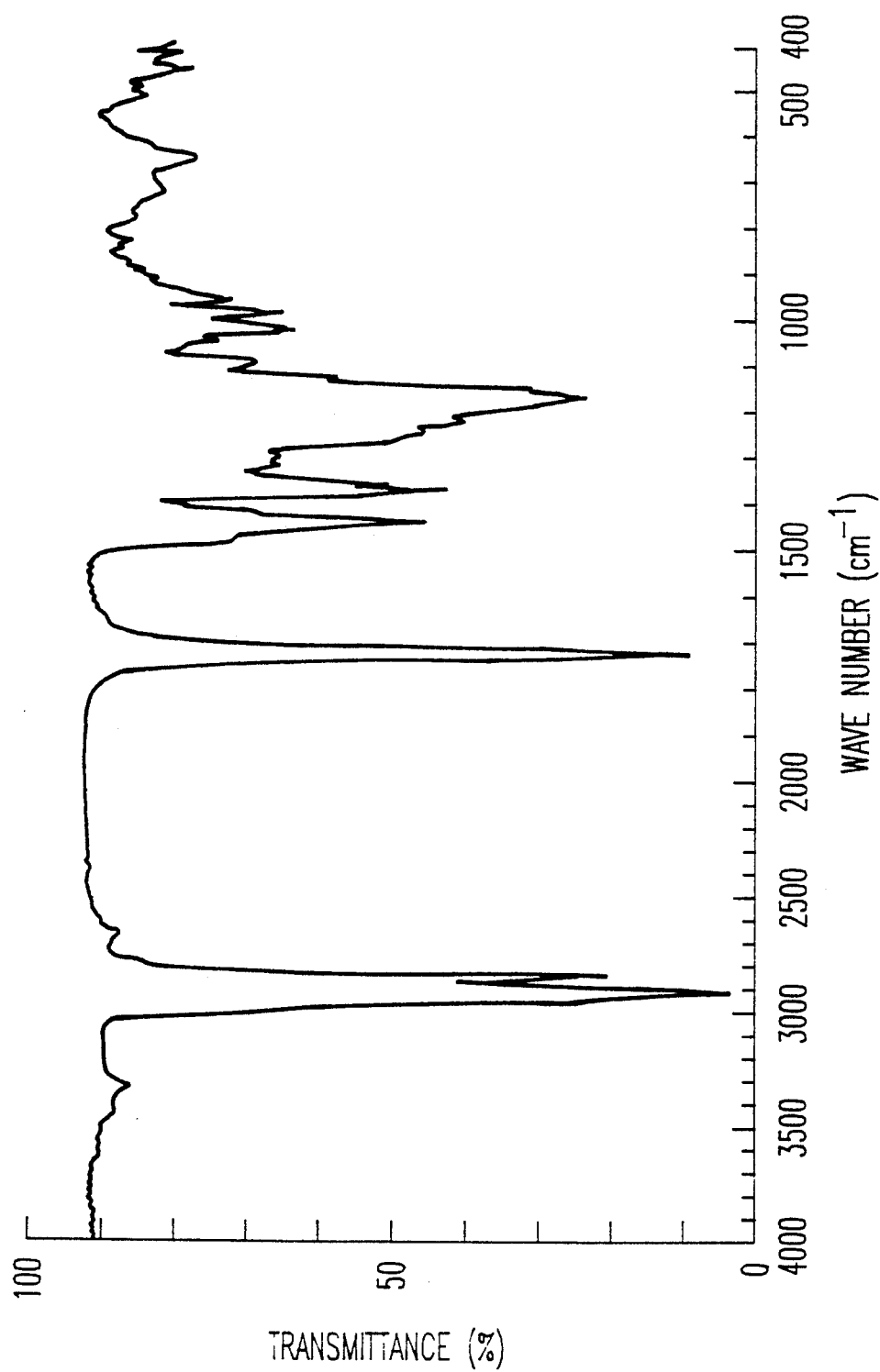

FIG. B1 is $^1$H-NMR spectrum for 3-cyclohexylmethyl-2,2,6,6-tetramethyl-4-piperidinol, Compound B prepared in Example B1;

FIG. B2 is a $^{13}$C-NMR spectrum by the proton decoupling method for 3-cyclohexylmethyl-2,2,6,6-tetramethyl-4-piperidinol, Compound B1 prepared in Example B1;

FIG. C1 is $^1$H-NMR spectrum for bis(3-cyclohexylmethyl-2,2,6,6-tetramethylpiperidine-4-yl) sebacate, Compound C15 prepared in Example C1;

FIG. C2 is a $^{13}$C-NMR by the proton decoupling method for bis(3-cyclohexylmethyl-2,2,6,6-tetramethylpiperidine, Compound C15 prepared in Example C1; and FIG. C3 is an IR absorption spectrum for bis(3-cyclohexylmethyl-2,2,6,6-tetramethylpiperidine-4-yl) sebacate, Compound C15 prepared in Example C1.

DETAILED DESCRIPTION OF PREFERRED EMBODIMENTS OF THE INVENTION

Outline of the Compounds

The piperidine derivatives in accordance with the present invention are represented by a formula [I] given hereinabove, and are thus classified into two classes.

The compounds of the first class are those of the formula [I] where $R^0$ is R—CO)$_n$, which are thus piperidinols.

The compounds of the second class are those of the formula [I] where $R^0$ is R—(CO)$_n$, which are thus esters of the piperidinols.

The piperidine derivatives in accordance with the present invention, irrespective of whether they are classified in the first or second class, have an amino group which is secondary where $R^1$ is H or is tertiary where $R^1$ is not H, whereby they can be in their salts.

It is thus to be understood that the term "piperidine derivatives" includes the derivatives in their salts, especially addition salts. Examples of acids to form the salts include inorganic acids, such as hydrohalogenic acids such as, e.g. hydrochloric acid; sulfuric acid, and phosphoric acid; and organic acids, such as lower alkane mono- or dicarboxylic acids such as formic acid, acetic acid, oxalic acid, and sulfonic acids such as toluenesulfonic acid.

The piperidine compounds in accordance with the invention of course possess reactivity as an alcohol, when $R^0$ is H, such as esterification to form esters, wherein the compounds of formula [I] in accordance with the present invention are an example of the esters.

Piperidinols

The piperidinols may also be classified into two subclasses.

The piperidinols of the first sub-group are those of the formula [I] where $R^3$ and $R^4$ contain unsaturation.

The piperidinols of the second sub-group are those of the formula [I] where the unsaturation in $R^3$ and $R^4$ of the first sub-group is hydrogenated.

In either group, the piperidinols of the formula [I] where $R^0$ is H are preferably those of the formula [I] where $R^{2'}$ is H.

1) The piperidinols of the first sub-group

The piperidinols of the formula [I] where $R^3$ and $R^4$ contain unsaturation of the first sub-group are those of the formula [I] where $R^3$ and $R^4$ in combination indicate a group =CH—$R^5$ or $R^3$ indicates a hydrogen atom and $R^4$ indicates a group —CH$_2$—$R^5$, where $R^5$ indicates an unsubstituted or $C_1$-$C_4$ alkyl-substituted phenyl group, or a 2-furyl group, $R^1$ and $R^2$ being defined above, and $R^{2'}$ being H.

The piperidinols of the first sub-class are those where $R^1$-$R^5$ are as follows.

$R^1$ is either one of a hydrogen atom, an alkyl group of 1 to 4 carbon atoms such as methyl and n-butyl, an acyl group of 2 to 7 carbon atoms such as acetyl and benzoyl, or arylalkyl group of 7 to 10 carbon atoms such as benzyl and 1-phenylethyl. $R^1$ is preferably a hydrogen atom or a methyl group from the viewpoint of production of the compounds, although all the $R^1$s referred to above may provide the compounds with improved photostabilizing capability.

$R^2$ is either one of a hydrogen atom, or an alkyl group of 1 to 4 carbon atoms such as a methyl group and a n-butyl group. $R^2$ is preferably a hydrogen atom or a methyl atom, a hydrogen atom being more preferable.

$R^3$ and $R^4$ are either one of (a) $R^3$ is a hydrogen atom and $R^4$ is a group —CH$_2$—$R^5$ or (b) $R^3$ and $R^4$ are in combination to form a group =CH—$R^5$, where $R^5$ is a phenyl group, $C_1$-$C_4$ o-, m- or p-alkyl-substituted phenyl such as a p-tolyl phenyl and p-t-butylphenyl or a 2-furyl group. $R^3$ and $R^4$ are preferably such that (i) $R^3$ is a hydrogen atom and $R^4$ is a benzyl, (ii) $R^3$ is a hydrogen atom and $R^4$ is a furfuryl, (iii) $R^3$ and $R^4$ in combination indicate a benzylidene group, or (iv) $R^3$ and $R^4$ in combination indicate furfurylidene group, and the compounds where $R^3$ is a hydrogen atom and $R^4$ is a benzyl group are more preferable.

Examples of the piperidinols of the first sub-class include:

(1) 3-Benzyl-2,2,6,6-tetramethyl-4-piperidinol, Compound A1, of a formula:

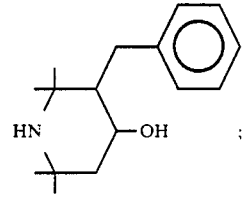

(2) 3-(4-Methylbenzyl)-2,2,6,6-tetramethyl-4-piperidinol, Compound A2, of a formula:

(3) 3-(2-Methylbenzyl)-2,2,6,6-tetramethyl-4-piperidinol, Compound A3, of a formula:

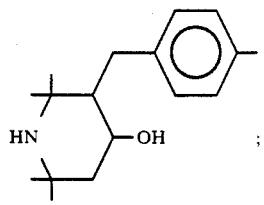

(4) 3-(4-t-Butylbenzyl)-2,2,6,6-tetramethyl-4-piperidinol, Compound A4, of a formula:

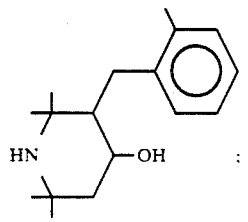

(5) 3-(2-t-Butylbenzyl)-2,2,6,6-tetramethyl-4-piperidinol, Compound A5, of a formula:

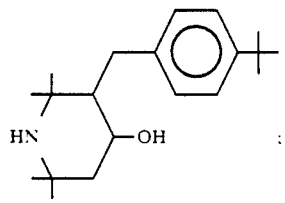

(6) 3-Benzyl-1,2,2,6,6-pentamethyl-4-piperidinol, Compound A6, of a formula:

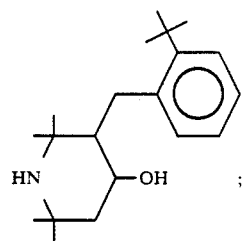

(7) 3-(4-Methylbenzyl)-1,2,2,6,6-pentamethyl-4-piperidinol, Compound A7, of a formula:

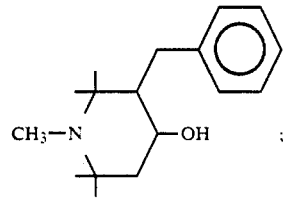

(8) 3-(2-Methylbenzyl)-1,2,2,6,6-pentamethyl-4-piperidinol, Compound A8, of a formula:

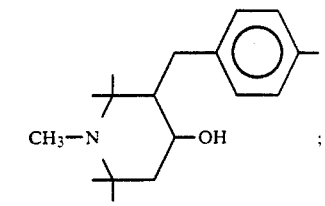

(9) 3-(4-t-Butylbenzyl)-1,2,2,6,6-pentamethyl-4-piperidinol, Compound A9, of a formula:

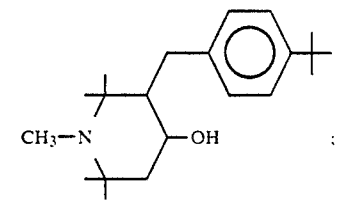

(10) 3-(2-t-Butylbenzyl)-1,2,2,6,6-pentamethyl-4-piperidinol, Compound A10, of a formula:

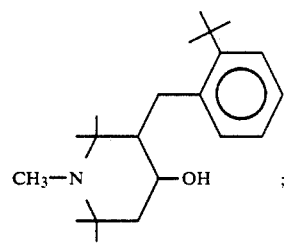

(11) 3-Furfuryl-2,2,6,6-tetramethyl-4-piperidinol, Compound A11, of a formula:

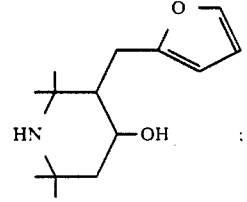

(12) 3-Furfuryl-1,2,2,6,6-pentamethyl-4-piperidinol, Compound A12, of a formula:

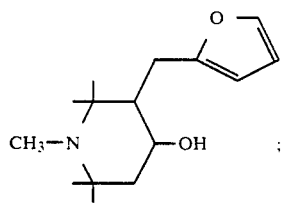

(13) 3-Benzylidene-2,2,6,6-tetramethyl-4-piperidinol, Compound A13, of a formula:

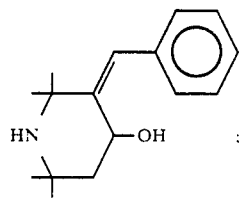

(14) 3-Benzylidene-1,2,2,6,6-pentamethyl-4-piperidinol, Compound A14, of a formula:

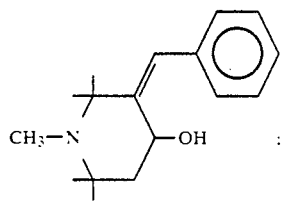

(15) 3-Furfurylidene-2,2,6,6-tetramethyl-4-piperidinol, Compound A15, of a formula:

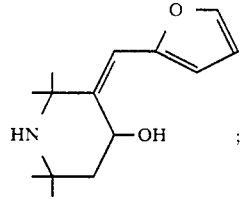

(16) 3-Furfurylidene-1,2,2,6,6-pentamethyl-4-piperidinol, Compound A16, of a formula:

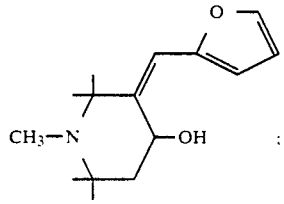

(17) 1-Benzyl-3-benzylidene-2,2,6,6-tetramethyl-4-piperidinol, Compound A17, of a formula:

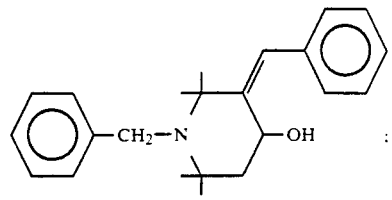

(18) 1-Acetyl-3-benzyl-2,2,6,6-tetramethyl-4-piperidinol, Compound A18, of a formula:

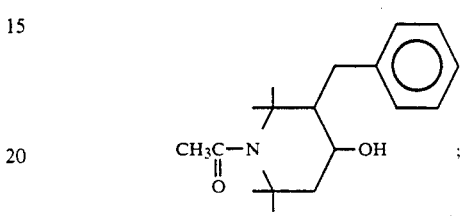

(19) 1-Benzoyl-3-benzyl-2,2,6,6-tetramethyl-4-piperidinol, Compound A19, of a formula:

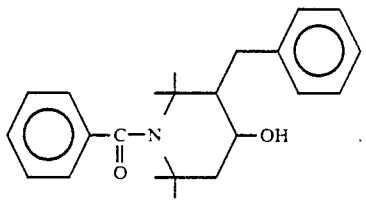

2) The piperidinols of the second sub-class

The piperidinols of the second sub-class correspond to hydrogenation products of the piperidinols of the first sub-class.

More particularly, the group $=CH-R^5$ or the group $-CH_2-R^5$ as $R^4$ when $R^3$ is H in the first sub-class is $-CH_2-R^5$ wherein $R^5$ is unsubstituted or $C_1-C_4$ alkyl-substituted cyclohexyl group or a tetrahydrofuryl group. $R^1$, $R^2$ and $R^{2'}$ have the same meaning in the first sub-class.

The piperidinols of the second sub-class are those where $R^1-R^5$ are as follows.

$R^1$ is either one of a hydrogen atom, an alkyl group of 1 to 4 carbon atoms such as methyl and n-butyl, an acyl group of 2 to 7 carbon atoms such as acetyl and benzyl, or an arylalkyl of 7 to 10 carbon atoms such as benzyl and 1-phenylethyl. $R^1$ is preferably a hydrogen atom or a methyl group from the viewpoint of production of the compounds, although all of the $R^1$s referred to above may provide the compounds with improved photostabilizing capability.

$R^2$ is either one of a hydrogen atom, or an alkyl group of 1 to 4 carbon atoms such as a methyl group and a n-butyl group. $R^2$ is preferably a hydrogen atom or a methyl group, a hydrogen atom being more preferable.

$R^3$ and $R^4$ are such that $R^3$ indicates a hydrogen atom and $R^4$ indicates a group $-CH_2-R^5$ where $R^5$ is unsubstituted or a $C_1-C_4$ alkyl-substituted cyclohexyl group or a tetrahydrofuryl group.

Examples of $R^5$ here include a cyclohexyl group, 2-methylcyclohexyl group, 4-methylcyclohexyl group, 2-ethylcyclohexyl group, 4-ethylcyclohexyl group, 2- isopropylcyclohexyl group, 4-isopropylcyclohexyl group, 2-t-butylcyclohexyl group, 4-t-butylcyclohexyl group and tetrahydrofuryl group, wherein a cyclohexyl group is preferable.

Examples of the piperidinols of the second sub-class include:

(1) 3-Cyclohexylmethyl-2,2,6,6-tetramethyl-4-piperidinol, Compound B1, of a formula:

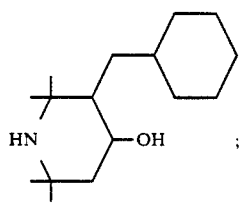

(2) 3-(4-Methylcyclohexylmethyl)-2,2,6,6-tetramethyl-4-piperidinol, Compound B2, of a formula:

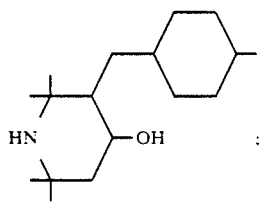

(3) 3-(2-Methylcyclohexylmethyl)-2,2,6,6-tetramethyl-4-piperidinol, Compound B3, of a formula:

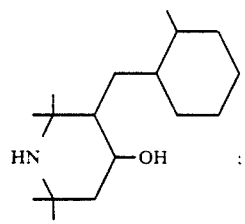

(4) 3-(4-t-Butylcyclohexylmethyl)-2,2,6,6-tetramethyl-4-piperidinol, Compound B4, of a formula:

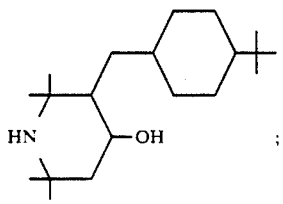

(5) 3-(2-t-Butylcyclohexylmethyl)-2,2,6,6-tetramethyl-4-piperidinol, Compound B5, of a formula:

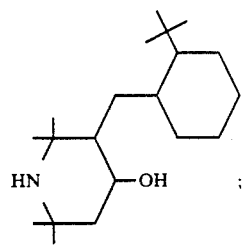

(6) 3-Tetrahydrofurfuryl-2,2,6,6-tetramethyl-4-piperidinol, Compound B6, of a formula:

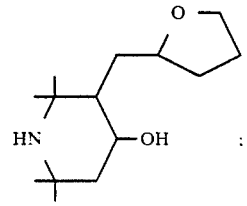

(7) 3-Cyclohexylmethyl-1,2,2,6,6-pentamethyl-4-piperidinol, Compound B7, of a formula:

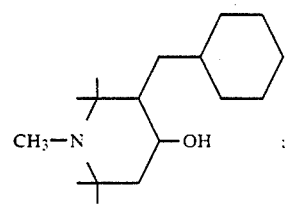

(8) 3-(4-Methylcyclohexylmethyl)-1,2,2,6,6-pentamethyl-4-piperidinol, Compound B8, of a formula:

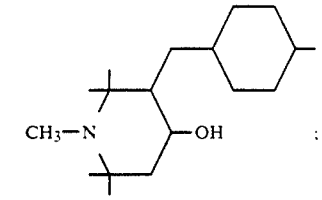

(9) 3-(2-Methylcyclohexylmethyl)-1,2,2,6,6-pentamethyl-4-piperidinol, Compound B9, of a formula:

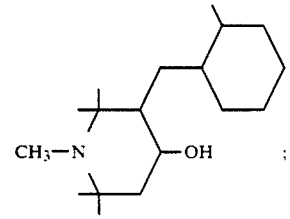

(10) 3-(4-t-Butylcyclohexylmethyl)-1,2,2,6,6-pentamethyl-4-piperidinol, Compound B10, of a formula:

(11) 3-(2-t-Butylcyclohexylmethyl)-1,2,2,6,6-pentamethyl-4-piperidinol, Compound B11, of a formula:

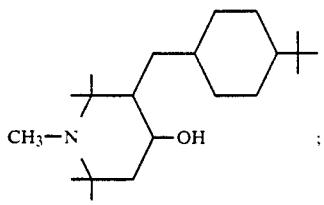

(12) 3-Tetrahydrofurfuryl-1,2,2,6,6-pentamethyl-4-piperidinol, Compound B12, of a formula:

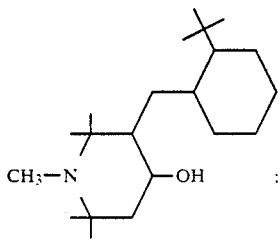

(13) 1-Benzyl-3-cyclohexylmethyl-2,2,6,6-tetramethyl-4-piperidinol, Compound B13, of a formula:

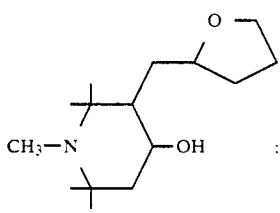

(14) 1-Acetyl-3-cyclohexylmethyl-2,2,6,6-tetramethyl-4-piperidinol, Compound B14, of a formula:

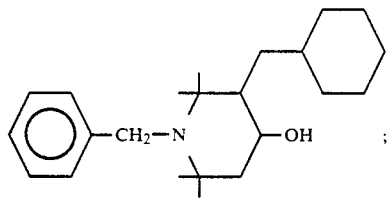

(15) 1-Benzoyl-3-cyclohexylmethyl-2,2,6,6-tetramethyl-4-piperidinol, Compound B15, of a formula:

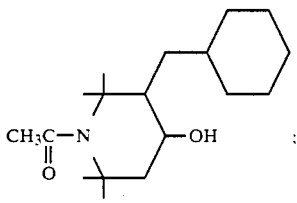

Piperidinyl Esters

The compounds of this class are those of the formula [I] where $R^0$ is $R \!\!-\!\!(CO)_{\overline{n}}$.

The compounds of formula [I] of this class are those where $R$–$R^5$ are as follows:

R indicates a saturated alkyl group, a saturated alkylene group or arylene group of 1 to 20 carbon atoms which can have 1 to 4 carboxylic group attached thereto.

The terms "alkyl group" and "alkylene group" herein include a cycloalkyl group and a cycloalkylene group, respectively, and "cycloalkylene group" includes those having a linear alkylene group such as

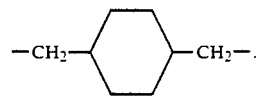

The term "arylene group" includes those having a linear alkylene group such as

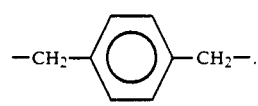

Preferred R is an alkyl group and an alkylene group, and examples of the preferred R, when indicated as R—COOH)$_n$, include: acetic acid, propionic acid, butyric acid, cyclopentane carboxylic acid, cyclohexane carboxylic acid, caprylic acid, 2-ethylhexanoic acid, lauric acid, stearic acid, bicyclo[2,2,1]heptane-2-carboxylic acid, malonic acid, succinic acid, maleic acid, glutaric acid, adipic acid, 1,2-cyclopentanedicarboxylic acid, 1,2-cyclohexanedicarboxylic acid, 1,4-cyclohexanedicarboxylic acid, sebacic acid, 1,10-decanedicarboxylic acid,bicyclo[2,2,1]heptane-2-carboxylic acid, 1,2,3-propanetricarboxylic acid, 1,2,3-butanetricarboxylic acid, 1,3,5-pentanetricarboxylic acid, 1,2,4-cyclohexanetricarboxylic acid, 1,3,5-cyclohexanetricarboxylic acid, 1,1,2,3-ethanetetracarboxylic acid, 1,1,2,3-propanetet-racarboxylic acid, 1,2,3,4-butanetetracarboxylic acid, 1,2,4,5-cyclohexanetetracarboxylic acid, and bicyclo[2,2,2]octane-2,3,5,6-tetracarboxylic acid.

$R^1$ is preferably a hydrogen atom or an alkyl group of 1 to 4 carbon atoms, and a hydrogen atom or a methyl group is more preferable.

$R^2$ and $R^{2'}$ are preferably a hydrogen atom or a methyl group, and a hydrogen atom is more preferable from the viewpoint of production of the compounds, although they all provide the compounds with improved photostabilizing capability.

$R^3$ and $R^4$ are preferably such that $R^3$ and $R^4$ in combination indicate (i) a benzylidene group or a $C_1$–$C_4$ alkyl-substituted benzylidene group or (ii) a cyclohexylmethylidene group or a $C_1-C_4$ alkyl-substituted cyclohexylmethylidene, or (iii) $R^3$ is a hydrogen atom and $R^4$ is a benzyl group or a $C_1-C_4$ alkyl-substituted benzyl or a cyclohexylmethyl group or a $C_1-C_4$ alkyl-substituted cyclohexylmethyl group.

In view of solubility in various organic material, especially polyolefins, and resistance to hydrolysis, of the compounds of this class, $R^3$ and $R^4$ are more preferably such that (a) $R^3$ and $R^4$ in combination are a benzylidene group or a $C_1-C_4$ alkyl-substituted benzylidene, or a cyclohexylmethylidene or a $C_1-C_4$ alkyl-substituted cyclohexylmethylidene, or (b) $R^3$ is a hydrogenatom and $R^4$ is a benzyl group or a $C_1-C_4$ alkyl-substituted benzyl group, or a cyclohexylmethyl or a $C_1-C_4$ alkyl-substituted cyclohexylmethyl group, and still more preferably $R^3$ is a hydrogen atom and $R^4$ is a benzyl group or a $C_1-C_4$ alkyl-substituted benzyl group, or a cyclohexylmethyl group or a $C_1-C_4$ substituted cyclohexylmethyl group.

n is an integer of 1 to 4, preferably 1 or 2.

Examples of the piperidinyl esters of this class include:

(1) 3-Benzyl-2,2,6,6-tetramethylpiperidin-4-yl cyclohexanecarboxylate, Compound C1, of a formula:

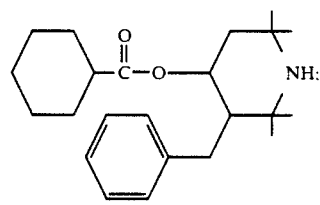

(2) 3-Cyclohexylmethyl-2,2,6,6-tetramethyl-2,2,6,6-tetramethylpiperidin-4-yl cyclohexanecarboxylate, Compound C2, of a formula:

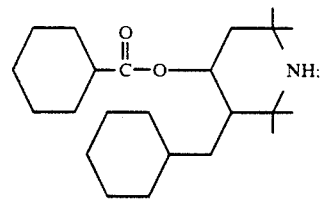

(3) 3-Benzylidene-2,2,6,6-tetramethylpiperidin-4-yl stearate, Compound C3, of a formula:

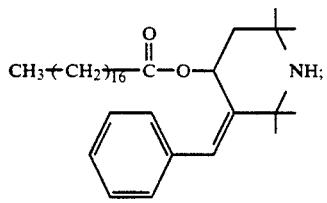

(4) 3-Benzyl-2,2,6,6-tetramethylpiperidin-4-yl stearate, Compound C4, of a formula:

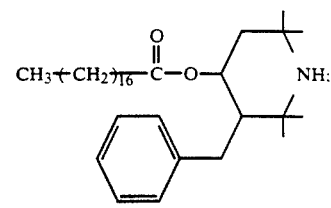

(5) 3-Cyclohexylmethyl-2,2,6,6-tetramethylpiperidin-4-yl stearate, Compound C5, of a formula:

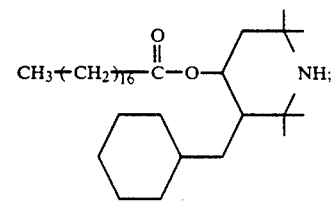

(6) 3-Cyclohexylmethyl-1,2,2,6,6-pentamethylpiperidin-4 -yl stearate, Compound C6, of a formula:

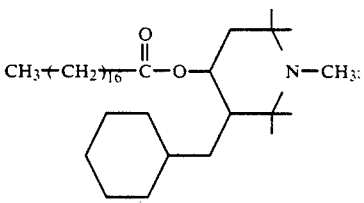

(7) Bis(3-benzyl-2,2,6,6-tetramethylpiperidin-4-yl) adipate, Compound C7, of a formula:

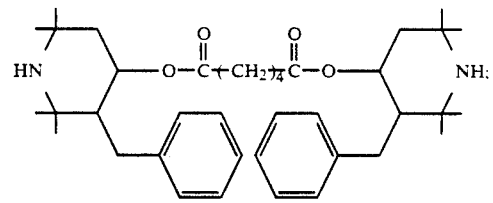

(8) Bis(3-cyclohexylmethyl-2,2,6,6-tetramethylpiperidin-4-yl) adipate, Compound C8, of a formula:

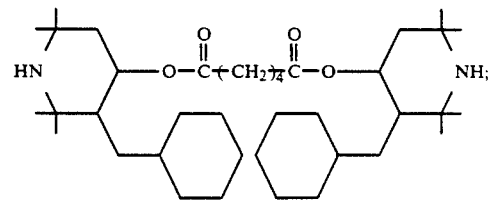

(9) Bis(3-benzylidene-2,2,6,6-tetramethylpiperidin-4-yl) dicarboxylate, Compound C9, of a formula:

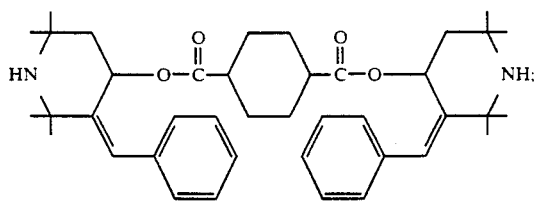

(10) Bis(3-benzyl-2,2,6,6-tetramethylpiperidin-4-yl) 1,4-cyclohexanedicarboxylate, Compound C10, of a formula:

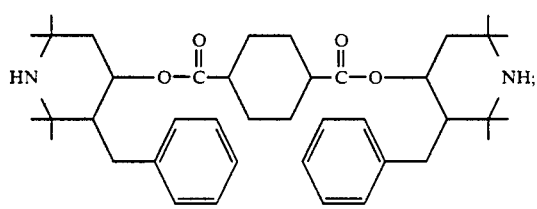

(11) Bis(3-cyclohexylmethyl-2,2,6,6-tetramethylpiperidin-4-yl) 1,4-cyclohexanedicarboxylate, Compound C11, of a formula:

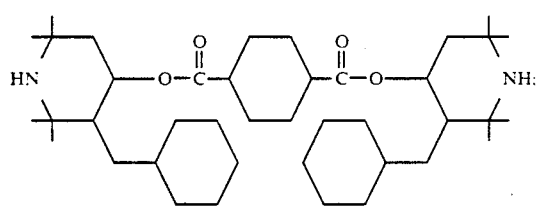

(12) Bis(3-cyclohexylmethyl-1,2,2,6,6-pentamethylpiperidin-4-yl) 1,4-cyclohexanedicarboxylate, Compound C12, of a formula:

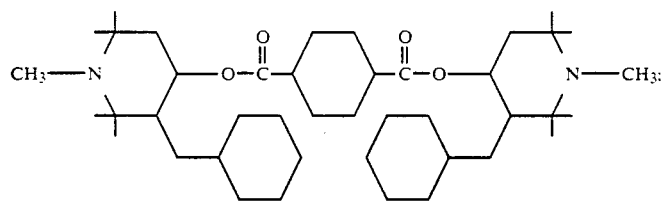

(13) Bis(3-benzylidene-2,2,6,6-tetramethylpiperidin-4-yl) sebacate, Compound C13, of a formula:

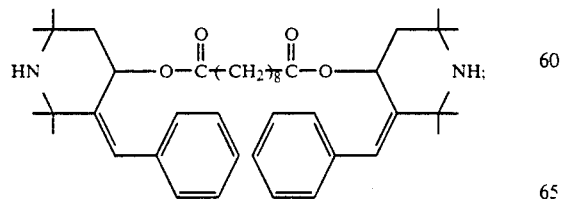

(14) Bis(3-benzyl-2,2,6,6-tetramethylpiperidin-4-yl) sebacate, Compound C14, of a formula:

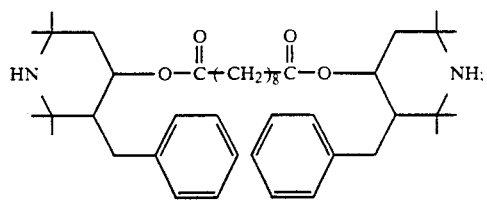

(15) Bis(3-cyclohexylmethyl-2,2,6,6-tetramethylpiperidin-4-yl) sebacate, Compound C15, of a formula:

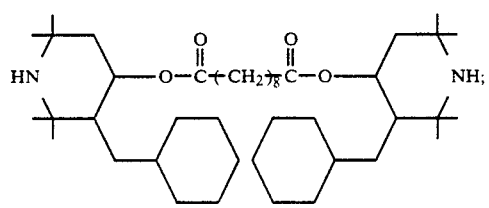

(16) Bis(3-cyclohexylmethyl-1,2,2,6,6-pentamethylpiperidin-4-yl) sebacate, Compound C16, of a formula:

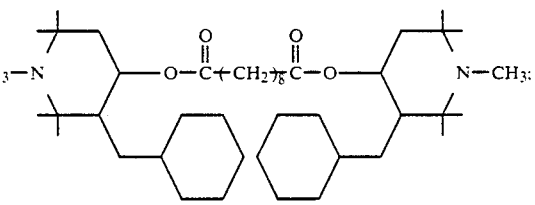

(17) Tris(3-benzyl-2,2,6,6-tetramethylpiperidin-4-yl) 1,2,3-propanetricarboxylate, Compound C17, of a formula:

(18) Tris(3-cyclohexylmethyl-2,2,6,6-tetramethylpiperidin-4-yl) 1,2,3-propanetricarboxylate, Compound C18, of a formula:

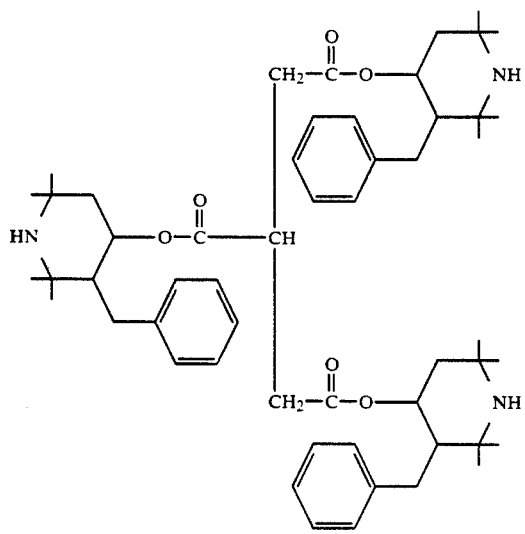

(19) Tris(3-benzylidene-2,2,6,6-tetramethylpiperidin-4-yl) 1,2,4-cyclohexanetricarboxylate, Compound C19, of a formula:

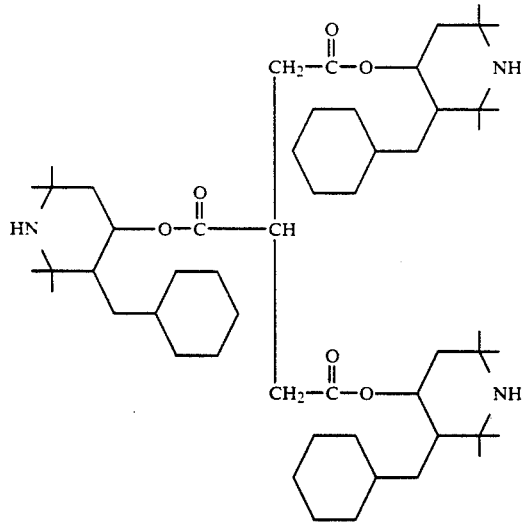

(20) Tris(3-benzyl-2,2,6,6-tetramethylpiperidin-4-yl) 1,2,4-cyclohexanetricarboxylate, Compound C20, of a formula:

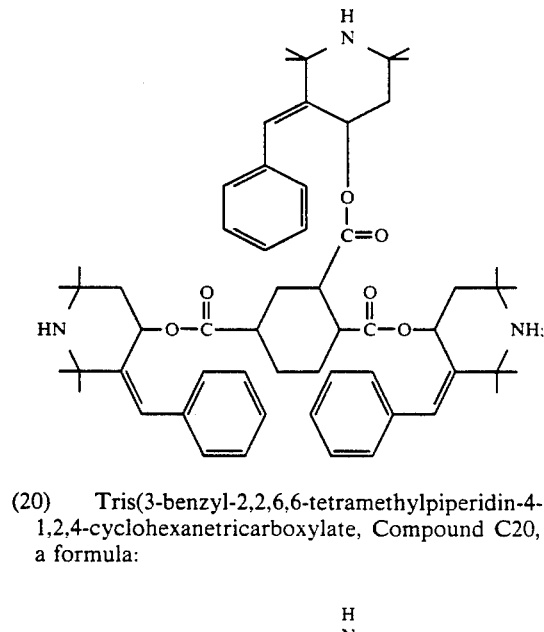

(21) Tris(3-cyclohexylmethyl-2,2,6,6-tetramethylpiperidin-4-yl) 1,2,4-cyclohexanetricarboxylate, Compound C21, of a formula:

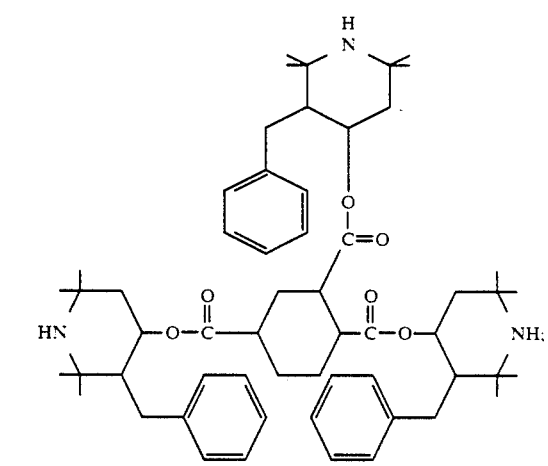

(22) Tris(3-cyclohexylmethyl-1,2,2,6,6-pentamethylpiperidin-4-yl) 1,2,4-cyclohexanetricarboxylate, Compound C22, of a formula:

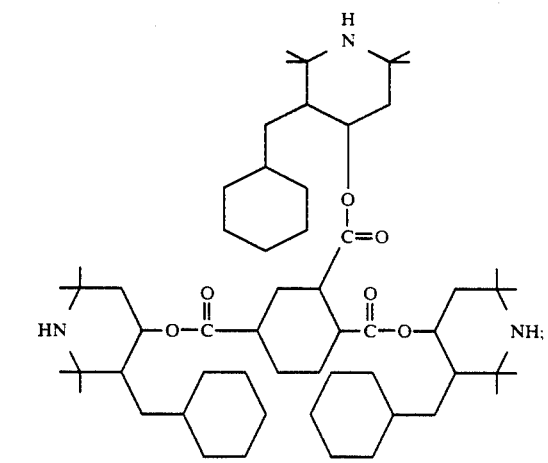

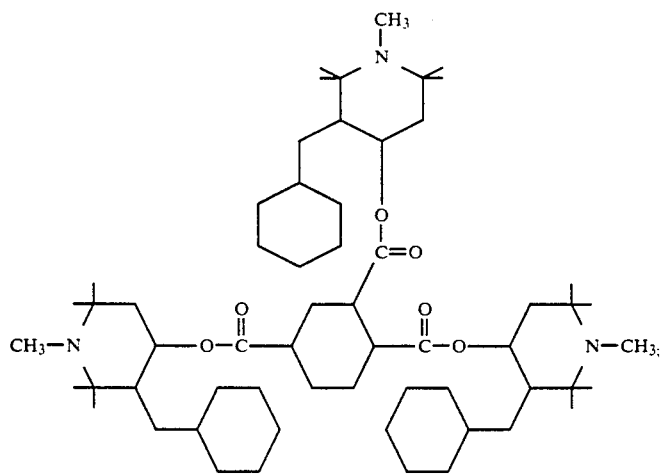
(23) Tetrakis(3-benzylidene-2,2,6,6-tetramethylpiperidin-4-yl) 1,2,3,4-butanetetracarboxylate, Compound C23, of a formula:
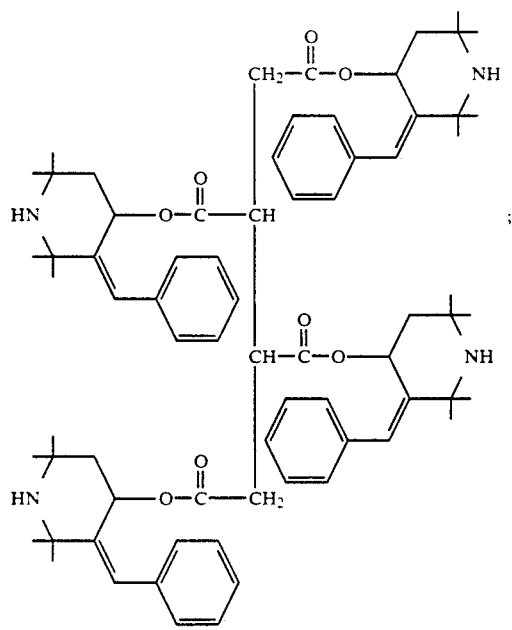
(24) Tetrakis(3-benzyl-2,2,6,6-tetramethylpiperidin-4-yl) 1,2,3,4-butanetetracarboxylate, Compound C24, of a formula:
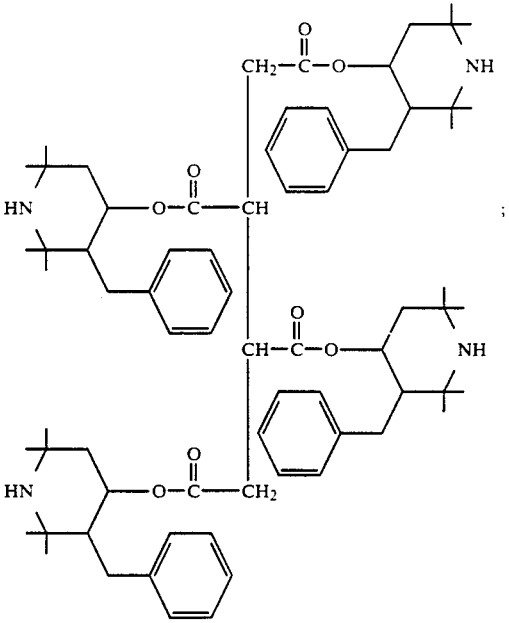
(25) Tetrakis(3-cyclohexylmethyl-1,2,2,6,6-pentamethylpiperidin-4-yl) 1,2,3,4-butanetetracarboxylate, Compound C25, of a formula:

(26) Tetrakis(3-cyclohexylmethyl-1,2,2,6,6-pentamethylpiperidin-4-yl) 1,2,3,4-butanetetracarboxylate, Compound C26, of a formula:

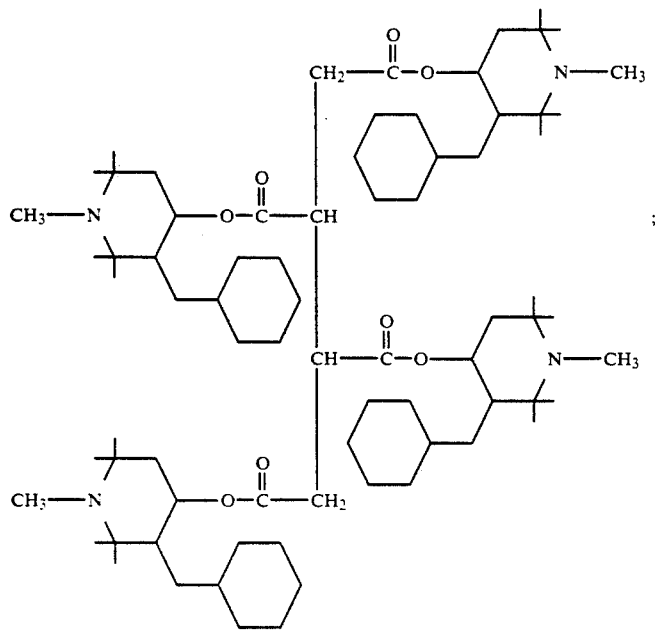

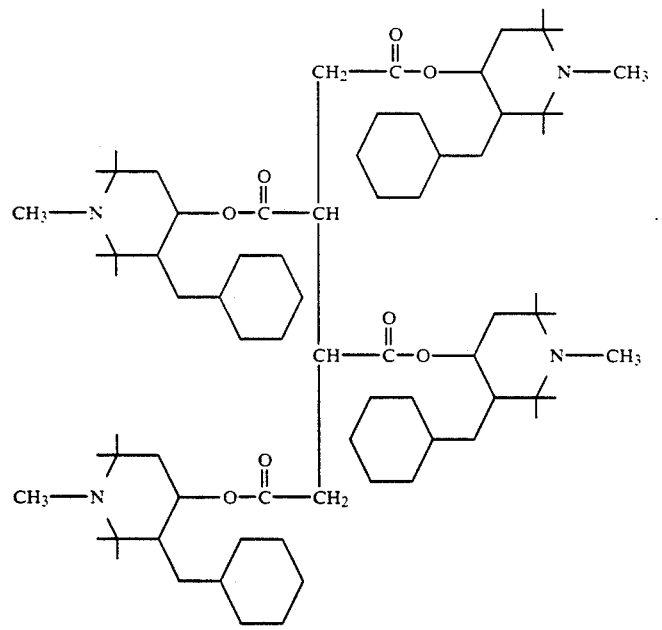

which will then be esterified into the compound of the formula [I] where $R^0$ is $R$-$(CO)_{\overline{n}}$.

(A) Production of the piperidinols

Production of the Compounds

The piperidine derivatives in accordance with the present invention are produced by any suitable methods in terms of forming of bonds or groups or substituents in the compounds.

An example of one of suitable methods is to hydrogenate a piperidinone of a formula [II] thereby to produce the compounds of the formula [I] where $R^0$ is H as set forth in the reaction scheme A given hereinbelow, Reaction scheme A:

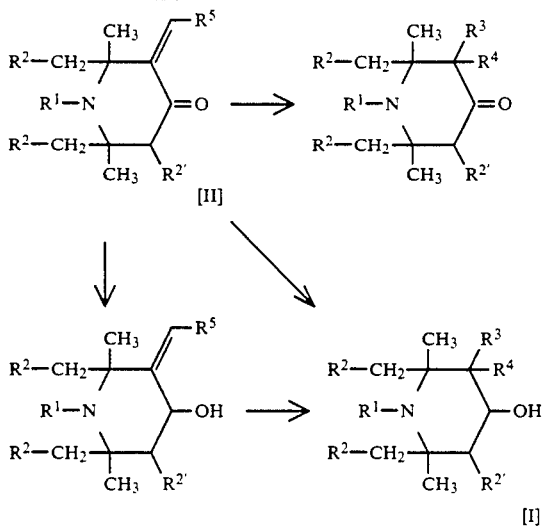

(1) Starting materials

The compound of a formula [II] used as a starting material in the reaction scheme A given above may be prepared by any suitable method such as that shown in Japanese Patent Publication Nos. 42987/1979 and 30307/1983.

More particularly, 3-benzylidene-2,2,6,6-tetramethyl-piperidinone, for example, is prepared from 2,2,6,6-tetramethyl-4-piperidinone and benzaldehyde.

The compounds of the formula [II] obtained in accordance with the method of the Japanese Patent Publications may be in the form of a mixture of the Z-isomer and the E-isomer.

The compound [II] in the scheme A is in the form of a mixture of the isomers, or alternatively either of the isomers separated from the mixture. Use of the mixture of the isomers may usually be preferred.

The hydrogenation may follow any of the convenient or conventional methods including the following methods.

(2) Catalytic hydrogenation

Preferable hydrogenation is catalytic hydrogenation, whereby the compound [II] which can be a mixture of Z- and E-isomers as shown above is hydrogenated in a vessel with hydrogen gas introduced into the vessel in the presence of a hydrogenation catalyst and an optional solvent or dispersant, and the hydrogenation product of the compound [II], namely the compound [I] of the present invention or the compound [I'] which is also a compound of the present invention falling in the scope of the formula [I], is separated from the catalyst and the solvent/dispersant used.

The catalytic hydrogenation may be carried out in a batchwise way, in a one-through method or in a recycling method.

The hydrogenation conditions comprise a reaction temperature may be −80° C. to 300° C., preferably 0° C. to 150° C., and a hydrogen pressure of 0.1 to 200 atms, preferably 1 to 150 atms when $R^3$ and $R^4$ contain unsaturation or a temperature of 0° C. to 300° C., preferably 50° C. to 200° C. and a hydrogen pressure of 1 to 300 atms, preferably 10 to 150 atms when $R^3$ and $R^4$ do not contain unsaturation.

Suitable solvent/dispersants may be selected depending on the type of reactants used or stability under reducing conditions, and are alcohols, esters or hydrocarbons, among which ethanol, isopropanol, tetrahydrofuran, dioxane and mineral spirit are preferable. These are used singly or in admixture.

The hydrogenation reaction is carried out in the presence of a hydrogenation catalyst Any hydrogenation catalysts which are known to have activity for hydrogenation can be used, including metals of the Group VIII of the Periodic Table such as palladium, platinum, ruthenium, rhodium, irridium, cobalt and nickel in the form of powder, a complex or oxide powder, or in the form supported on a support/carrier such as activated carbon, silica or alumina in an amount of 0.5 to 20% by weight.

Preferable among these are ruthenium on activated carbon, ruthenium on alumina, rhodium on activated carbon, rhodium on alumina and Raney nickel.

The amount of a catalyst is, usually, 0.01 to 10% by weight, preferably 0.05 to 5% by weight, of the compound [II].

(3) Chemical reduction

The piperidine derivatives in accordance with the present invention can alternatively be produced by a chemical reduction of the compound [II] with a reducing agent.

Examples of the reducing agent include metal hydrides such as sodium borohydride, lithium aluminum hydride, boron hydrides such as diborane, hydrazine and ammonia, which are used usually in an amount capable of supplying hydrogen in an amount of 1 to 1.2 times the stoichiometric amount of hydrogen required.

The reaction is carried out usually in a solvent/dispersant which dissolves the reactants and the reducing agents and is stable under the reducing conditions, such as alcohols, ethers and hydrocarbons.

The reaction is carried out usually at a temperature of −80° C. to 150° C., preferably 0° C. to 100° C.

It is possible to conduct the reaction in the presence of an additive in order to improve reaction velocity and/or selectivity, including alkaline or alkaline earth metal hydroxides such as LiOH, NaOH and KOH, stannous or stannic compounds such as $SnCl_2$, $SnCl_4$ and $SnO_2$, and $H_2O$, in an amount of 0.1 to 5% by weight.

The catalytic hydrogenation (2) and the chemical reduction (3) can be combined to produce the piperidine derivatives in accordance with the present invention of the formula [I] where $R^0$ is H.

(B) Production of piperidinyl esters

The piperidinyl esters in accordance with the present invention are produced by any suitable methods in terms of forming of bonds or groups or substituents in the compound.

An example of one of suitable methods is to esterify a compound of the formula [I] where $R^0$ is H with a carboxylic acid of $R+COOH)_n$ which may be in the form of a carboxylic acid, an ester with a lower alkanol, an acid anhydride or an acid halide.

Preferable method comprises ester interchange where the carboxylic acid is used in the form of an ester with a lower alkanol such as methanol as shown in the scheme B given below.

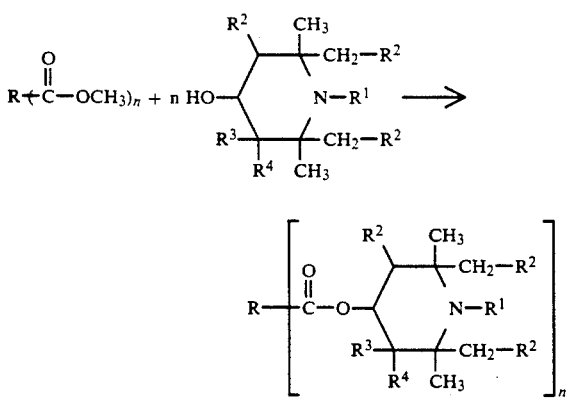

The ester interchange reaction is usually carried out in the presence of a basic catalyst such as lithiumamide, or sodium methoxide and an organic solvent such as hexane, heptane, toluene or dioxane. The reaction temperature may be 0° C. to a reflux temperature, preferably 50° C. to 150° C.

Utility/Use of the Compounds

The compounds of the formula [I] in accordance with the present invention are useful as compounds having a hindered amine structure in stabilization, especially photostabilization, of various organic materials as such or as derivatives thereof such that the hydroxyl group, when $R^0$ is H, is utilized is reacted with a mono- or poly (such as di- or tri-) basic carboxylic acid into esters, the compounds of the formula [I] where $R^0$ is $R-CO)_n$ being particular examples of such esters, with a mono- or poly (such as di- or tri-) isocyanate into methanes The compounds of the formula [I] where $R^1$ is H and $R^0$ is H are aminoalcohol compounds and can thus be converted, upon reaction with a dicarboxylic acid, into poly (ester/amide)s which can also be used as a stabilizer and the like.

More particularly, the piperidinols of the formula [I] where $R^0$ is H in accordance with the present invention have a secondary or a tertiary amino group as well as a secondary alcoholic hydroxyl group, and are thus equipped with reactivities inherent in these functional groups. For instance, the compounds may thus be converted into esters or amides, and particularly, when the carboxylic acid is a polycarboxylic acid, into bis esters or polyesteramides of a high molecular weight when the polycarboxylic acid is a dicarboxylic acid. Examples of the dicarboxylic acid include those of 2 to 16, preferably 2 to 10 carbon atoms including aliphatic acids, alicyclic such as cyclohexanecarboxylic acid and aromatic carboxylic acid such as terephthalic acid. It goes without saying that the esterification can be conducted so that one or both of the reactants is in its functional derivative, for instance the dicarboxylic acid is in the form of a diester with a lower alkanol to form an ester through ester interchange.

Organic materials to be stabilized against light by incorporation thereinto of the piperidine derivatives of the formula [I] in accordance with the present invention include a lot of materials. Representative group of such organic materials is high polymeric materials such as, for example, poly α-olefins such as low-density polyethylenes, medium density polyethylenes, linear low-density polyethylenes, polypropylenes, polybutene-1, α-olefin copolymers such as ethylene-propylene random or block copolymers, ethylene-butene-1 copolymers, and copolymers of an α-olefin with a vinyl monomer such as polypropylenes modified with maleic anhydride through grafting, which are as such or in admixture thereof. Most typical polymeric material is polypropylene.

Other polymeric materials other than those referred to above can also be photostabilized by the piperidine derivatives in accordance with the present invention, which include polyvinyl chlorides, polymethacrylic resins, styrene-based resins, e.g. polystyrenes, high impact polystyrenes, ABS resins and AES resins, polyester resins such as polyethylene terephthalate and polybutylene terephthalate, polyamides, polycarbonates, polyacetals, polyethylene oxides, polyphenylene ethers, polysulfones, polyurethanes and unsaturated polyester resins.

Naturally occurring organic materials are other examples of organic materials stabilized against photodegradation by incorporation thereinto of the piperidine derivatives in accordance with the present invention, which include naturally occurring polymeric materials, e.g. celluloses, rubbers, proteins or their derivatives such as cellulose acetates, mineral oils, animal and vegetable fat and oil, and waxes.

The piperidine derivatives in accordance with the present invention are used solely as a stabilizer against photodegradation of organic materials, but they can be used in combination with another photostabilizer upon necessity.

The following examples are given only for describing the present invention in more detail.

EXAMPLE A1

3-Benzyl-2,2,6,6-tetramethyl-4-piperidinol, Compound A1

Into a 50 ml-flask equipped with a thermometer, a gas inlet, a cooling tube and a magnetic stirrer were introduced 2.0 g (8.2 mmol) of 3-Z-benzylidene-2,2,6,6-tetramethyl-4-piperidinone and 25 ml of ethanol, and then nitrogen gas through the gas inlet under stirring. Upon the flask being filled with nitrogen, 0.10 g of a Pd-on-carbon catalyst containing 10% of Pd, supplied by N.E. Chemcat K.K., Japan was introduced under nitrogen into the flask and the content in the flask was agitated. After ca. 2 minutes, hydrogen was introduced, and hydrogenation was carried out for 2 hours at room temperature under atmospheric pressure.

Introduction of hydrogen was then stopped, and nitrogen was introduced into the flask through the gas inlet to drive the hydrogen off the flask, and the solution in the flask was then filtered to remove the catalyst used.

The solution thus obtained was introduced a 100 ml-flask equipped with a thermometer, a cooling tube and a magnetic stirrer, and 0.75 g (20 mmol) of $NaBH_4$ was gradually introduced under agitation of the solution. After one hour, 10% aq. HCl was introduced so that the pH of the solution became 6, and an excess amount of $NaBH_4$ was removed. To the solution was then added 10% aq. NaOH so that the pH of the solution became 8 and the solution was agitated thoroughly. The solution was then subjected to reduced pressure to distill the ethanol off.

The white solid matter precipitated was extracted with 100 ml of diethylether, and the extract obtained was washed three times with 20 ml of water. To the solution obtained was added 10 g of magnesium sulfate, and after 2 hours of standing, the solution was filtered and concentrated to give 1.85 g of a white solid product. The white solid product obtained gave, upon recrystallization from its acetonitrile solution, 1.7 g (yield: 84%) of the title compound as white crystals.

The physical data of this compound is as follows.
(1) Melting point: 140.0° C.
(2) Molecular weight: M$^+$ =247 (m/e)
(3) $^1$H-NMR (CDCl$_3$) δ(ppm) (FIG. A1): 0.75–0.95 (bs, 1H), 1.00–1.45 (m, 13H), 1.48–1.75 (m, 2H), 2.60–2.90 (m, 2H), 3.80–4.10 (m, 1H), 7.05–7.35 (m, 5H)
(4) $^{13}$C-NMR (CDCl$_3$) δ(ppm) (FIG. A2): 27.7, 31.6, 32.3, 32.9, 34.1, 44.4, 49.4, 50.8, 53.2, 66.3, 125.6, 128.3, 129.0, 142.0

EXAMPLE A2

3-Z-Benzylidene-2,2,6,6-tetramethyl-4-piperidinol, Compound A13

Into a 200 ml-flask equipped with a thermometer, a cooling tube and a magnetic stirrer were introduced 10.0 g (41 mmol) of 3-Z-benzylidene-2,2,6,6-tetramethyl-4-piperidinone and 100 ml of methanol, and the content was agitated into a homogeneous solution. After the solution was cooled to 0° to 5° C. in an ice bath, 3.8 g (100 mmol) of NaBH$_4$ was gradually introduced into the solution so that the temperature of the solution was maintained no higher than 10° C. and the reaction was continued for 3 hours. Then, 10% aqueous HCl was added to the solution so that the pH became 6, and the excess NaBH$_4$ was removed. To the solution was added 10% aqueous NaOH so that the pH became 8, and the solution, after thorough agitation, was subjected to reduced pressure to distill the methanol off.

The white solid matter precipitated was extracted with 200 ml of diethylether, and the extract obtained was washed three times with 30 ml of water. To the solution obtained was added 10 g of magnesium sulfate, and after 2 hours of standing, the solution was filtered and concentrated to give 9.5 g of a white solid product. The white solid product obtained gave, upon recrystallization from its acetonitrile solution, 8.7 g (yield: 86%) of the title compound as white crystals.

The physical data of this compound is as follows.
(1) Melting point: 136.9° C.
(2) Molecular weight: M$^+$ =245 (m/e)
(3) $^1$H-NMR (CDCl$_3$) δ(ppm): 0.91–1.68 (m, 14H), 1.93–2.09 (m, 1H), 2.99–3.20 (m, 1H), 4.62–4.82 (m, 1H), 6.48–6.52 (s, 1H), 7.10–7.42 (m, 5H)
(4) $^{13}$C-NMR (CDCl$_3$) δ(ppm): 33.1, 33.4, 35.3, 35.6, 42.4, 49.0, 54.6, 66.3, 124.9, 126.7, 128.2, 128.8, 137.0, 147.9

EXAMPLE A3

3-Benzyl-1,2,2,6,6-pentamethyl-4-piperidinol, Compound A6

Into a 100 ml-flask equipped with a thermometer, a cooling tube, a dropping funnel and a magnetic stirrer were added 3.7 g of 3-benzyl-2,2,6,6-tetramethyl-4-piperidinol prepared in Example A1 above, 30 ml of dioxane and 0.78 g of fumic acid, and the content in the flask was heated to 80° C. When the temperature of the content was at a constant level, 2.44 g of 37% aqueous formaldehyde in which 10 ml of dioxane had been dissolved was introduced gradually through the dropping funnel, and the content of the flask was heated at the same temperature under agitation for 8 hours. The temperature was then lowered to room temperature, 10% aqueous NaOH was added so that the pH became to 7, and the solution was subjected to extraction with 150 ml of diethylether. The extract obtained was washed three times with 30 ml of water, 10 g of magnesium sulfate and the solution was kept standing for 2 hours, and the solution was filtered and concentrated to give 3.3 g (yield: 83%) of the title compound as a white solid product.

The physical data of this compound is as follows.
(1) Melting point: 84.3° C.
(2) Molecular weight: M$^+$ =261 (m/e)
(3) $^1$H-NMR (CDCl$_3$) δ(ppm): 0.89–2.02 (m, 16H), 2.19–2.45 (s, 3H), 2.73–3.07 (d, 2H), 3.88–4.14 (m, 1H), 7.02–7.61 (m, 5H)
(4) $^{13}$C-NMR (CDCl$_3$) δ(ppm): 24.9, 25.8, 26.3, 28.2, 29.5, 31.6, 45.8, 52.4, 54.1, 58.2, 66.0, 125.4 128.2, 129.1, 143.2

EXAMPLE A3

Bis(3-benzyl-2,2,6,6-tetramethyl-4-piperidyl) sebacate, Compound A1 ′ (C14)

To a 300 ml-flask equipped with a thermometer, a Dien-Stark cooling tube and a magnetic stirrer were introduced 5.93 g (24 mmol) of 3 benzyl-2,2,6,6-tetramethyl-4-piperidinol, Compound A1, prepared in Example A1, 2.30 g (10 mmol) of dimethyl sebacate, 0.1 g of NaOCH$_3$ as a catalyst and 200 ml of heptane, and the content of the flask was heated at a reflux temperature for ca. 8 hours to carry out the reaction.

The content of the flask was then cooled to room temperature, 200 ml of diethylether was added thereto, and the mixture was washed with 50 ml of water three times.

The organic layer obtained was dried by 10 g of magnesium sulfate added thereto for ca. 3 hours. The magnesium sulfate was then filtered off, and the solvent was distilled off in vacuo to give 8.04 g of a white wax product. The white wax product obtained was purified by alumina column chromatography, the solvent being chloroform, to give 5.20 g (yield: 79.0%) of the title compound as a white wax product.

The physical properties of the product are as follows.
(1) Molecular weight: M$^+$ =660 (m/e)
(2) $^1$H-NMR (CDCl$_3$) δ(ppm): 0.90–1.48 (m, 36H), 1.52–1.78 (m, 6H), 1.80–1.96 (dd, 2H), 2.18–2.46 (t, 4H), 2.48–2.89 (m, 4H), 4.92–5.09 (m, 2H), 7.06–7.43 (m, 10H)
(3) $^{13}$C-NMR (CDCl$_3$) δ(ppm): 25.0, 26.8, 29.1, 29.2, 30.5, 32.8, 33.1, 34.4, 34.9, 40.6, 49.3, 49.7, 49.8, 53.1, 69.8, 126.0, 128.4, 128.9, 140.8, 173.0

EVALUATION A1

To 100 parts by weight of powder of polypropylene having an intrinsic viscosity of 1.9 determined at 135° C. in tetralin and a content of the isotactic fraction of 98% were added 0.2 parts by weight of the sample prepared in Examples A1, A2 and A3, respectively, and 0.1 part by weight of tetrakis[3-(3,5-di-tert-butyl-4-hydroxyphenyl) propionyloxymethyl] methane, and the mixtures were thoroughly mixed by a mixer, and the mixture was kneaded and extruded from an extruder of a cylinder temperature of 260° C. and an extruder diameter of 20 mm into pellets.

The pellets were press-molded at 230° C. into a sheet of 0.5 mm thick to form a test piece, test pieces 1, 2 and 3.

Other pieces were prepared from resin compositions which were the same as those used in forming test pieces 1, 2 and 3 except that, in place of the piperidine derivatives, 3-Z-benzylidene-2,2,6,6-tetramethyl-4-piperidinone, comparative compound (i), prepared in accordance with the method disclosed in Japanese Patent Publication Nos. 42987/1979 and 30307/1983 and LS770 which was a commercially available hindered amine photostabilizer produced and supplied by Sankyo Co., Ltd., Japan, were respectively used.

These test pieces were subjected to a photostabilization test by a xenone weather-O-meter, Model 65/XW-WR, manufactured by Atlas Corp. under irradiation with light at the black panel temperature of 80° C. until the test pieces became deteriorated, and the time required until the deterioration was measured and recorded in Table A1 given below.

TABLE A1

| No. | Additive | Time until deterioration. Hr. |
| --- | --- | --- |
| 1a | — | 100 |
| 2a | Comp. compd. (i) | 110 |
| 3a | Compound A1 | 430 |
| 4a | Compound A13 | 240 |
| 5a | Compound A1' | 520 |
| 6a | LS770 | 320 |

As is evident from the results set forth in Table A1, the piperidine derivatives in accordance with the present invention are improved photostabilization, namely elongation of the time until the deterioration, irrespective of whether they are piperidinols or a sebacate thereof in Nos. 3a, 4a and 5a than the reference compounds in Nos. 1a, 2a and 6a.

EVALUATION A2

The pellets obtained in Evaluation A1 were subjected to determination of the yellowness index, YI. The yellowness index was determined by Color Tester manufactured by Suga Testing Machine Co., Ltd., Japan.

The results obtained are set forth in Table A2.

TABLE A2

| Sample tested | YI |
| --- | --- |
| Compound A1 | 8.9 |
| Compound A13 | 7.1 |
| Comp. Compd. (i) | 17.9 |
| LS770 | 9.1 |
| Compound A1' | 11.8 |

EVALUATION A3

The test pieces containing Compound A1' and LS770 were subjected to weathering test by a weather-O-meter for 300 hours.

No breeding was observed for the test piece containing Compound A1', but breeding was observed for the test piece containing LS770 in that the sheet had white powdery material adhering on its surface, which was wiped off to show that it was a breed.

EXAMPLE B1

3-Cyclohexylmethyl-2,2,6,6-tetramethyl-4-piperidinol, Compound B1

Into a pressure-resistant vessel of a volume of 260 ml equipped with an induction stirrer, a gas inlet and a thermocouple were introduced 20.0 g (82.2 mmol) of 3-Z-benzylidene-2,2,6,6-tetramethyl-4-piperidinone and 150 ml of ethanol. The vessel was purged with nitrogen under stirring, and 1.0 g of 5% Rh-on-carbon catalyst (N.E. Chemcat) was introduced and the vessel was sealed 2 minutes after, hydrogen gas under 70 atm was introduced through the gas inlet and the reaction was carried out at 65° C. for 5 hours.

The vessel was then cooled down to room temperature, and nitrogen was introduced through the gas inlet into the vessel to expel the hydrogen in the vessel, whereupon the vessel was opened and the solution obtained was filtered to remove catalyst.

The solution obtained was charged into a 500 ml-flask equipped with a thermometer, a cooling tube and a magnetic stirrer, and 3.0 g (80 mmol) of NaBH$_4$ was gradually added under stirring 5 hours after, a 10% aqueous HCl was added to the solution so that the pH became 6, and an excess amount of NaBH$_4$ was removed. A 10% aqueous NaOH was then added to the solution so that the pH became 8, and after ample stirring, the solution was subjected to a reduced pressure to distill off the ethanol. The white solid material precipitated was extracted with 1000 ml of diethyl ether, and the extract was washed with 100 ml of water 5 times. 20 g of magnesium sulfate was added to the solution obtained, and after standing for ca. 2 hours, the solution was filtered and concentrated to give 19.8 g of a white solid, which was recrystallized from hexane to give 17.5 g (yield: 84%) of the title compound as white crystals.

The physical properties of the product are as follows.

(1) Melting point: 144.8° C.

(2) Molecular weight: M$^+$ = 253 (m/e)

(3) $^1$H-NMR (CDCl$_3$) δ(ppm) (FIG. B1): 0.47–1.83 (m, 29H), 4.09–4.28 (m, 1H)

(4) $^{13}$C-NMR (CDCl$_3$) δ(ppm) (FIG. B2): 26.7, 26.9, 28.6, 32.3, 32.9, 33.0, 33.2, 33.7, 34.5, 36.7, 43.7, 45.4, 50.1, 53.7, 67.6

EXAMPLE B2

3-Cyclohexylmethyl-1,2,2,6,6-pentamethyl-4-piperidinol, Compound B7

Into a 100 ml-flask equipped with a thermometer, a cooling tube, a dropping funnel and a magnetic stirrer were introduced 3.8 g (15 mmol) of 3-cyclohexylmethyl-2,2,6,6-tetramethyl-4-piperidinol prepared in Example B1, 70 ml of dioxane and 0.78 g (17 mmol) of formic acid, and the content of the flask was heated to 80° C. When the temperature of the content of the flask was constant, 2.44 g (30 mmol) of 37% aqueous formaldehyde dissolved in 20 ml of dioxane was added gradually through the dropping funnel, followed by heating at the temperature for 10 hours. The content of the flask was cooled to room temperature, and 5% aqueous NaOH was added so that the pH became 8, followed by extraction with 200 ml of diethylether. The extract obtained was washed with 30 ml of water 3 times, 10 g of magnesium sulfate was added and, after it was kept standing for ca. 2 hours, the solution was filtered and concentrated to give 3.95 g (yield: 98%) of the title compound as a white solid product.

The physical properties of the product obtained are as follows.

(1) Melting point: 95.1° C.

(2) Molecular weight: M$^+$ = 267 (m/e)

(3) $^1$H-NMR (CDCl$_3$) δ(ppm): 0.74–1.86 (m, 28H), 2.24 (s, 3H), 3.94–4.18 (m, 1H)

(4) $^{13}$C-NMR (CDCl$_3$) δ(ppm): 24.6, 25.8, 26.1, 26.8, 27.0, 28.5, 30.6, 33.2, 33.9, 34.3, 37.7, 45.7, 47.6, 54.5, 58.4, 67.0, 67.4

EXAMPLE B3

Bis(3-cyclohexylmethyl-2,2,6,6-tetramethylpiperidin-4-yl) sebacate, Compound B1' (C15)

Into a 200 ml-flask equipped with a thermometer, a Dien Stark cooling tube and a magnetic stirrer were introduced 4.05 g (16 mmol) of 3-cyclohexylmethyl-2,2,6,6-tetramethyl-4-piperidinol, 1.61 g (7 mmol) of dimethyl sebacate, 0.1 g of LiNH$_2$ catalyst and 120 ml of heptane, and the reaction was carried out at a reflux temperature for ca. 8 hours.

The content of the flask was then cooled to room temperature, 200 ml of diethylether was added, and the solution was washed with 50 ml of water 3 times. The organic layer was then dried by 10 g of magnesium sulfate added thereto for ca. 3 hours. The solution was filtered to remove the magnesium sulfate, and subjected to a reduced pressure to distill the solvent used to give 5.34 g of a colorless transparent liquid product, which was purified by alumina chromatography, the solvent being chloroform, to give 4.34 g (yield: 92.1%) of the title compound as a colorless transparent liquid product.

The physical properties of the product obtained are as follows.

(1) Molecular weight: M$^+$ = 672 (m/e)
(2) $^1$H-NMR (CDCl$_3$) δ(ppm): 0.70–1.80 (m, 70H), 2.29 (t, 4H), 5.20–5.30 (m, 2H)
(3) $^{13}$C-NMR (CDCl$_3$) δ(ppm): 25.0, 26.2, 26.4, 26.6, 27.1, 29.1, 31.2, 32.6, 33.0, 33.6, 33.9, 34.4, 34.9, 35.5, 40.6, 43.7, 49.3, 53.0, 70.2, 173.3

EVALUATION B1

To 100 parts by weight of powder of polypropylene having an intrinsic viscosity of 1.9 determined at 135° C. in tetralin and a content of the isotactic fraction of 98% were added 0.2 parts by weight of the sample prepared in Examples B1 and 0.1 part by weight of tetrakis[3-(3,5-di-tert-butyl-4-hydroxyphenyl) propionyloxymethyl] methane, and the mixture was thoroughly mixed by a mixer, and the mixture was kneaded and extruded from an extruder of a cylinder temperature of 260° C. and an extruder diameter of 20 mm into pellets.

The pellets were press-molded at 230° C. into a sheet of 0.5 mm thick to form a test piece, test pieces 1 and 2.

Other pieces were prepared from resin compositions which were the same as those used in forming test pieces 1 and 2 except that, in place of the piperidine derivatives, 3-Z-benzylidene-2,2,6,6-tetramethyl-4-piperidinone, comparative compound (i), prepared in accordance with the method disclosed in Japanese Patent Publication Nos. 42987/1979 and 30307/1983 and LS770 which was a commercially available hindered amine photostabilizer produced and supplied by Sankyo Co., Ltd., Japan, were respectively used.

These test pieces were subjected to a photostabilization test by a xenone weather-o-meter, Model 65/XW-WR, manufactured by Atlas Corp. under irradiation with light at the black panel temperature of 80° C. until the test pieces became deteriorated, and the time required until the deterioration was measured and recorded in Table B1 given below.

TABLE B1

| No. | Additive | Time until deterioration, Hr. |
|---|---|---|
| 1b | — | 155 |
| 2b | Comp. compd. (i) | 170 |
| 3b | Compound B1 | 470 |
| 4b | Compound B1' | 700 |
| 5b | LS770 | 495 |

As is evident from the results set forth in Table A1, the piperidine derivatives in accordance with the present invention are improved photostabilization, namely elongation of the time until the deterioration, irrespective of whether they are piperidinols or a sebacate thereof in Nos. 3b and 4b than the reference compounds in Nos. 1b, 2b and 5b.

EVALUATION B2

The pellets obtained in Evaluation A1 were subjected to determination of the yellowness index, YI. The yellowness index was determined by Color Tester manufactured by Suga Testing Machine Co., Ltd., Japan.

The results obtained are set forth in Table B2.

TABLE B2

| Sample tested | YI |
|---|---|
| Comp. Compd. (i) | 10.4 |
| Compound B1 | 1.99 |
| Compound B1' | 2.28 |
| LS770 | 2.06 |

EVALUATION A3

The test pieces containing Compound B1' and LS770 were subjected to weathering test by a weather-O-meter for 300 hours.

No breeding was observed for the test piece containing Compound B1', but breeding was observed for the test piece containing LS770 in that the sheet had white powdery material adhering on its surface, which was wiped off to show that it was a breed.

EXAMPLE C1

Bis(3-cyclohexylmethyl-2,2,6,6-tetramethyl-4-piperidinyl) sebacate, Compound C15 which is equal to Compound B1'

Into a 300 ml-flask equipped with a Dien Stark cooling tube were introduced 8.9 g (35 mmol) of 3-cyclohexylmethyl-4-hydroxy-2,2,6,6-tetramethyl-4-piperidine, 3.5 g (15 mmol) of dimethyl sebacate, 0.2 g (4 mmol) of LiNH$_2$ catalyst and 200 ml of heptane, and the reaction was carried out at a reflux temperature (100° C.) for 10 hours wherein methanol was distilled off azeotropically with n-heptane.

The content of the flask was then cooled to room temperature, 150 ml of diethylether was added, and the solution was washed with 50 ml of water 2 times. The organic layer was then dried by anhydrous magnesium sulfate added thereto. The solution was filtered to remove the magnesium sulfate and concentrated to give 10.8 g of a pale yellow transparent viscous liquid product, which was purified by alumina chromatography, the solvent being chloroform, to give 9.3 g (yield: 92%) of the title compound as a colorless transparent viscous liquid product.

The physical properties of the product obtained are as follows.

(1) $^1$H-NMR (CDCl$_3$) δ(ppm) (FIG. C1): 0.70–1.80 (m, 70H), 2.29 (t, 4H), 5.20–5.30 (m, 2H)

(2) $^{13}$C-NMR (CDCl$_3$) δ(ppm) (FIG. C2): 25.0, 26.2, 26.4, 26.6, 27.1, 29.1, 31.2, 32.6, 33.0, 33.6, 33.9, 34.4, 34.9, 35.5, 40.6, 43.7, 49.3, 53.0, 70.2, 173.3

(3) IR (KBr) Wave number [cm$^{-1}$] (FIG. C3): 2920, 2850, 1732, 1448, 1377, 1362, 1249, 1223, 1171, 1127, 1093, 1022, 979, 955, 720, 652, 459

EXAMPLE C2

Bis(3-cyclohexylmethyl-1,2,2,6,6-pentamethylpiperidin-4-yl) sebacate, Compound C16

The procedure set forth in Example C1 was followed except for the use of 9.3 g (35 mmol) of 3-cyclohexylmethyl-4-hydroxy-1,2,2,6,6-pentamethylpiperidine in place of 3-cyclohexylmethyl-4-hydroxy-2,2,6,6-tetramethylpiperidine to produce 11.1 g of pale yellow viscous liquid product, which was purified by alumina gel chromatography, the solvent being chloroform to give 9.8 g (yield: 93%) of the title compound as a colorless transparent viscous liquid product.

The physical properties of the product are as follows.

(1) $^1$H-NMR (CDCl$_3$) δ(ppm): 0.75–1.85 (m, 68H), 2.18–2.33 (m, 10H), 5.17–5.25 (m, 2H)

(2) $^{13}$C-NMR (CDCl$_3$) δ(ppm): 23.4, 24.9, 25.9, 26.4, 26.7, 27.5, 27.7, 28.3, 29.2, 33.4, 33.5, 34.1, 34.9, 36.8, 41.9, 45.3, 53.9, 57.9, 69.9, 173.4

EXAMPLE C3

Bis(3-cyclohexylmethyl-2,2,6,6-tetramethylpiperidin-4-yl) cyclohexanecarboxylate, Compound C11

The procedure set forth in Example C1 was followed except for the use of 3.0 g (15 mmol) of 1,4-cyclohexanedicarboxylate in place of dimethyl sebacate to produce 9.5 g of pale yellow viscous liquid product, which was purified by alumina gel chromatography, the solvent being chloroform to give 8.6 g (yield: 89%) of the title compound as a colorless transparent viscous liquid product.

The physical properties of the product are as follows.

(1) $^1$H-NMR (CDCl$_3$) δ(ppm): 0.75–2.53 (m, 68H), 5.22–5.30 (m, 2H)

(2) $^{13}$C-NMR (CDCl$_3$) δ(ppm): 26.1, 26.3, 26.5, 26.8, 28.0, 28.1, 28.2, 30.9, 32.8, 33.7, 34.2, 34.6, 35.2, 40.7, 43.1, 43.8, 49.0, 52.7, 70.2, 174.9

EXAMPLE C4

Bis(3-benzyl-2,2,6,6-tetramethylpiperidin-4-yl) sebacate, Compound C14 which is equal to Compound A1'

The procedure set forth in Example C1 was followed except for the use of 8.7 g (35 mmol) of 3-benzyl-4-hydroxy-2,2,6,6-tetramethylpiperidine in place of 3-cyclohexylmethyl-4-hydroxy-2,2,6,6-tetramethylpiperidine to produce 10.5 g of pale yellow viscous liquid product, which was purified by alumina gel chromatography, the solvent being chloroform to give 8.7 g (yield: 88%) of the title compound as a colorless transparent viscous liquid product.

The physical properties of the product are as follows.

(1) $^1$H-NMR (CDCl$_3$) δ(ppm): 1.02–1.44 (m, 40H), 1.58–1.77 (m, 6H), 1.87 (dd, 2H), 2.34 (t, 4H) 2.52–2.63 (m, 2H), 2.76–2.85 (m, 2H), 4.92–5.03 (m, 2H), 7.08–7.34 (m, 10H)

(2) $^{13}$C-NMR (CDCl$_3$) δ(ppm): 24.9, 26.8, 29.2, 30.5, 32.8, 33.2, 34.4, 34.9, 40.6, 49.3, 49.8, 53.1, 69.8, 126.0, 128.4, 128.9, 140.8, 173.0

EXAMPLE C5

3-Benzyl-2,2,6,6-tetramethylpiperidin-4-yl sebacate, Compound C4

The procedure set forth in Example C4 was followed except for the use of 4.5 g (15 mmol) of methyl sebacate in place of dimethyl sebacate to produce 8.2 g of pale yellow viscous liquid product, which was purified by alumina gel chromatography, the solvent being chloroform to give 7.1 g (yield: 92%) of the title compound as a colorless transparent viscous liquid product.

The physical properties of the product are as follows.

(1) $^1$H-NMR (CDCl$_3$) δ(ppm): 0.88 (s, 3H), 1.03–1.46 (m, 41H), 1.62–1.75 (m, 3H), 1.86 (dd, 2H), 1.34 (t, 2H), 2.51–2.62 (m, 1H), 2.74–2.82 (m, 1H), 4.91–4.98 (m, 1H), 7.05–7.31 (m, 5H)

(2) $^{13}$C-NMR (CDCl$_3$) δ(ppm): 14.1, 22.7, 25.0, 26.9, 29.3, 29.4, 29.5, 29.7, 30.6, 31.9, 32.9, 33.3, 34.5, 34.9, 40.7, 49.1, 50.0, 52.9, 69.8, 126.0, 128.4, 128.9, 140.9, 173.0

EXAMPLE C6

Bis(3-benzyl-2,2,6,6-tetramethylpiperidin-4-yl) 1,4-cyclohexanedicarboxylate, Compound C10

The procedure set forth in Example C4 was followed except for the use of 3.0 g (15 mmol) of dimethyl 1,4-cyclohexanedicarboxylate in place of dimethyl sebacate to produce 9.3 g of pale yellow viscous liquid product, which was purified by alumina gel chromatography, the solvent being chloroform to give 8.0 g (yield: 85%) of the title compound as a colorless transparent viscous liquid product.

The physical properties of the product are as follows.

(1) $^1$H-NMR (CDCl$_3$) δ(ppm): 0.95–1.90 (m, 36H), 2.12–2.40 (m, 6H), 2.48–2.63 (m, 2H), 2.73–2.85 (m, 2H), 4.92–5.05 (m, 2H), 7.05–7.33 (m, 10H)

(2) $^{13}$C-NMR (CDCl$_3$) δ(ppm): 26.3, 26.9, 28.1, 28.2, 28.3, 28.4, 30.7, 32.8, 33.2, 34.5, 40.7, 43.1, 49.1, 50.0, 52.9, 70.0, 126.0, 128.5, 128.8, 140.8, 174.5

EXAMPLE C7

Bis(3-benzylidene-2,2,6,6-tetramethylpiperidin-4-yl) sebacate, Compound C13

The procedure set forth in Example C1 was followed except for the use of 8.6 g (35 mmol) of 3-benzylidene-4-hydroxy-2,2,6,6-tetramethylpiperidine in place of 3-cyclohexylmethyl-4-hydroxy-2,2,6,6-tetramethylpiperidine to produce 9.7 g of pale yellow viscous liquid product, which was purified by alumina gel chromatography, the solvent being chloroform to give 8.5 g (yield: 87%) of the title compound as a colorless transparent viscous liquid product.

The physical properties of the product are as follows.

(1) $^1$H-NMR (CDCl$_3$) δ(ppm): 1.06–1.75 (m, 40H), 2.06 (dd, 2H), 2.25 (t, 4H), 5.81–5.85 (m, 2H), 6.68 (s, 2H), 7.08–7.34 (m, 2H)

(2) $^{13}$C-NMR (CDCl$_3$) δ(ppm): 24.9, 29.0, 32.3, 32.5, 32.9, 33.4, 34.9, 41.0, 48.8, 54.5, 69.1, 127.1, 127.9, 128.3, 128.4, 136.8, 142.8, 172.5

EXAMPLE C8

3-Benzylidene-2,2,6,6-tetramethylpiperidin-4-yl) stearate, Compound C3

The procedure set forth in Example C7 was followed except for the use of 4.5 g (15 mmol) of methyl stearate in place of dimethyl sebacate to produce 7.8 g of pale yellow viscous liquid product, which was purified by alumina gel chromatography, the solvent being chloroform to give 6.9 g (yield: 96%) of the title compound as a colorless transparent viscous liquid product.

The physical properties of the product are as follows.

(1) $^1$H-NMR (CDCl$_3$) δ(ppm): 0.88 (t, 3H), 1.11-1.71 (m, 44H), 2.04 (dd, 1H), 2.23 (t, 2H), 5.82-5.87 (m, 1H), 6.65 (s, 1H), 7.09-7.32 (m, 5H)

(2) $^{13}$C-NMR (CDCl$_3$) δ(ppm): 14.1, 22.7, 24.9, 29.1, 29.3, 29.4, 29.5, 29.7, 31.9, 32.5, 33.0, 33.5, 34.7, 41.0, 48.4, 54.1, 69.0, 126.9, 127.6, 128.1, 128.4, 136.8, 143.1, 172.0

EXAMPLE C9

Bis(3-benzylidene-2,2,6,6-tetramethylpiperidin-4-yl) 1,4-cyclohexanedicarboxylate, Compound C9

The procedure set forth in Example C7 was followed except for the use of 3.0 g (15 mmol) of dimethyl 1,4-cyclohexanedicarboxylate in place of dimethyl sebacate to produce 9.3 g of pale yellow viscous liquid product, which was purified by alumina gel chromatography, the solvent being chloroform to give 7.7 g (yield: 82%) of the title compound as a colorless transparent viscous liquid product.

The physical properties of the product are as follows.

(1) $^1$H-NMR (CDCl$_3$) δ(ppm): 1.08-1.57 (m, 30H), 1.65-1.77 (m, 2H), 1.96-2.28 (m, 8H), 5.79 (t, 2H), 6.69 (s, 2H), 7.03-7.35 (m, 10H)

(2) $^{13}$C-NMR (CDCl$_3$) δ(ppm): 28.1, 32.5, 32.6, 33.1, 33.6, 41.2, 43.0, 48.5, 54.2, 69.4, 127.9, 128.3, 128.4, 136.9, 143.0, 174.1

EVALUATION C1

To 100 parts by weight of powder of polypropylene having an intrinsic viscosity of 1.9 determined at 135° C. in tetralin and a content of the isotactic fraction of 98% were added 0.2 parts by weight of the sample prepared in Examples C1-C9 and 0.1 part by weight of tetrakis[3-(3,5-di-tert-butyl-4-hydroxyphenyl) propionyloxymethyl] methane, and the mixture was thoroughly mixed by a mixer, and the mixture was kneaded and extruded from an extruder of a cylinder temperature of 260° C. and an extruder diameter of 20 mm into pellets.

The pellets were press-molded at 230° C. into a sheet of 0.5 mm thick to form a test piece, test pieces 1-9.

Another piece was prepared from resin compositions which was the same as those used in forming test piece 9 except that, in place of the piperidine derivatives, bis(2,2,6,6-tetramethylpiperidine) sebacate (LS770) was used.

These test pieces were subjected to a photostabilization test by a xenone weather-o-meter, Model 65/XW-WR, manufactured by Atlas Corp. under irradiation with light at the black panel temperature of 80° C. until the test piece became deteriorated, and the time required until the deterioration was measured and recorded in Table C1 given below.

TABLE C1

| No. | Additive | Time until deterioration, Hr. |
|---|---|---|
| 1c | — | 100 |
| 2c | Bis(2,2,6,6-tetramethylpiperidin-4-yl) sebacate (LS770) | 640 |
| 3c | Bis(3-cyclohexylmethyl-2,2,6,6-tetramethylpiperidin-4-yl) sebacate (Compound C15) | 900 |
| 4c | Bis(3-cyclohexylmethyl-1,2,2,6,6-pentamethylpiperidin-4-yl) sebacate (Compound C16) | 920 |
| 5c | Bis(3-cyclohexylmethyl-2,2,6,6-tetramethylpiperidin-4-yl) 1,4-cyclohexanedicarboxylate (Compound C11) | 900 |
| 6c | Bis(3-benzyl-2,2,6,6-tetramethylpiperidin-4-yl) sebacate (Compound C14) | 890 |
| 7c | 3-Benzyl-2,2,6,6-tetramethylpiperidin-4-yl stearate (Compound C4) | 720 |
| 8c | Bis(3-benzyl-2,2,6,6-tetramethylpiperidin-4-yl) 1,4-cyclohexanedicarboxylate (Compound C10) | 760 |
| 9c | Bis(3-benzylidene-2,2,6,6-tetramethylpiperidin-4-yl) sebacate (Compound C13) | 650 |
| 10c | 3-Benzylidene-2,2,6,6-tetramethylpiperidin-4-yl stearate (Compound C3) | 660 |
| 11c | Bis(3-benzylidene-2,2,6,6-tetramethylpiperidin-4-yl) 1,4-cyclohexanedicarboxylate (Compound C9) | 650 |

As is evident from the results set forth in Table A1, the piperidine derivatives in accordance with the present invention are improved photostabilization, namely elongation of the time until the deterioration.

What is claimed is:

1. A compound represented by the formula:

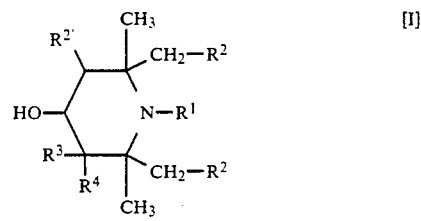

wherein

R$^1$ indicate a hydrogen atom, an alkyl group having 1 to 4 carbon atoms, a benzoyl group, a phenylalkylcarbonyl group, a phenylalkyl group all having 1 to 4 carbon atoms in said alkyl, or an alkylcarbonyl group having 1 to 6 carbon atoms in said alkyl;

R$^2$ and R$^{2'}$ respectively are a hydrogen atom or an alkyl group having 1 to 4 carbon atoms;

R$^3$ and R$^4$ in combination form a group =CH—R$^5$ wherein R$^5$ is either a substituted or non-substituted phenyl group or a substituted or non-substituted cyclohexyl group, the substituent being an alkyl group having 1 to 4 carbon atoms, or a 2-furyl group or a tetrahydrofuryl group, or R$^3$ indicates a hydrogen atom and R$^4$ indicates —CH$_2$—R$^5$ wherein R$^5$ is either a substituted to a non-substituted cyclohexyl group, the substituent being an alkyl having 1 to 4 carbon atoms or a tetrahydrofuryl group.

2. The compound of claim 1, wherein R$^3$ and R$^4$ in combination form a benzylidene group or a furfurylidene group.

3. The compound as claimed in claim 1, wherein R$^3$ is a hydrogen atom and R$^4$ is a cyclohexylmethyl group.

4. The compound of claim 1, wherein R$^3$ and R$^4$, in combination form a group =CH—R$^5$, wherein R$^5$ is defined as in claim 1.

* * * * *